US011096582B2

(12) United States Patent
Mitchell et al.

(10) Patent No.: US 11,096,582 B2
(45) Date of Patent: Aug. 24, 2021

(54) VASCULAR ACCESS DEVICES, SYSTEMS, AND METHODS FOR MONITORING PATIENT HEALTH

(71) Applicant: Veris Health Inc., New York, NY (US)

(72) Inventors: James D. Mitchell, Walnut Creek, CA (US); Theodore C. Johnson, Lake Forest Park, WA (US); Andrew Thoreson, Orono, MN (US)

(73) Assignee: Veris Health Inc., New York, NY (US)

( * ) Notice: Subject to any disclaimer, the term of this patent is extended or adjusted under 35 U.S.C. 154(b) by 0 days.

(21) Appl. No.: 16/197,083

(22) Filed: Nov. 20, 2018

(65) Prior Publication Data

US 2020/0155003 A1    May 21, 2020

(51) Int. Cl.
*A61B 5/00* (2006.01)
*A61B 5/0205* (2006.01)
(Continued)

(52) U.S. Cl.
CPC .......... *A61B 5/0031* (2013.01); *A61B 5/0008* (2013.01); *A61B 5/0205* (2013.01); *A61B 5/1118* (2013.01); *A61M 39/0247* (2013.01); *A61B 5/0006* (2013.01); *A61B 5/0022* (2013.01); *A61B 5/0024* (2013.01); *A61B 5/112* (2013.01); *A61B 5/14532* (2013.01);
(Continued)

(58) Field of Classification Search
CPC ... A61B 5/0031; A61B 5/0008; A61B 5/0205; A61B 5/1118; A61B 5/142; A61M 39/0247; A61M 2039/0258; A61M 2039/0267; A61M 2039/027
See application file for complete search history.

(56) References Cited

U.S. PATENT DOCUMENTS 4,834,720 A    5/1989  Blinkhorn
4,846,191 A    7/1989  Brockway et al.
(Continued)

FOREIGN PATENT DOCUMENTS

AU          691877 B2    5/1998
CA          2757836 C    5/2017
(Continued)

OTHER PUBLICATIONS

Dubovitskaya, et al., "Secure and Trustable Electronic Medical Records Sharing using Blockchain", AMAI Annual Symposium Proceedings Achive, Jan. 1, 2017, pp. 650-659.
(Continued)

*Primary Examiner* — Eric D. Bertram
*Assistant Examiner* — Pamela M. Bays
(74) *Attorney, Agent, or Firm* — Fortem IP, LLP; Katrina Henrikson

(57) ABSTRACT

The present technology relates to vascular access devices, systems, and methods configured to monitor a patient's health. In some embodiments, the vascular access device may include a sensing element, and the system of the present technology may be configured to obtain physiological measurements of the patient via the sensing element, determine at least one physiological parameter based on the physiological measurement, compare the at least one physiological parameter to a predetermined threshold, and, based on the comparison, provide an indication of the patient's health.

14 Claims, 9 Drawing Sheets

(51) Int. Cl.
  *A61B 5/11* (2006.01)
  *A61M 39/02* (2006.01)
  *A61B 5/145* (2006.01)
(52) U.S. Cl.
  CPC .............. *A61M 2039/027* (2013.01); *A61M 2039/0258* (2013.01); *A61M 2039/0267* (2013.01)

(56) References Cited

U.S. PATENT DOCUMENTS

| | | |
|---|---|---|
| 4,861,341 A | 8/1989 | Woodburn |
| 4,929,236 A | 5/1990 | Sampson |
| 5,167,638 A | 12/1992 | Felix et al. |
| 5,185,003 A | 2/1993 | Brethauer |
| 5,281,205 A | 1/1994 | McPherson |
| 5,360,407 A | 11/1994 | Leonard et al. |
| 5,399,168 A | 3/1995 | Wadsworth et al. |
| 5,423,334 A | 6/1995 | Jordan |
| 5,476,460 A | 12/1995 | Montalvo |
| 5,558,641 A | 9/1996 | Glantz et al. |
| 5,613,945 A | 3/1997 | Cai et al. |
| 5,620,419 A | 4/1997 | Lui et al. |
| 5,637,102 A | 6/1997 | Tolkoff et al. |
| 5,743,873 A | 4/1998 | Cai et al. |
| 5,833,654 A | 11/1998 | Powers et al. |
| 5,951,512 A | 9/1999 | Dalton |
| 5,989,216 A | 11/1999 | Johnson et al. |
| 6,086,555 A | 7/2000 | Eliasen et al. |
| 6,113,572 A | 9/2000 | Gailey et al. |
| 6,213,973 B1 | 4/2001 | Eliasen et al. |
| 6,478,783 B1 | 11/2002 | Moorehead |
| 6,562,023 B1 | 5/2003 | Marrs et al. |
| 6,650,939 B2 | 11/2003 | Taepke et al. |
| 6,804,558 B2 | 10/2004 | Haller et al. |
| 6,847,844 B2 | 1/2005 | Sun et al. |
| 6,922,592 B2 | 7/2005 | Thompson et al. |
| 6,997,914 B2 | 2/2006 | Smith et al. |
| 7,037,273 B2 | 5/2006 | Zhu et al. |
| 7,069,086 B2 | 6/2006 | Von Arx |
| 7,070,591 B2 | 7/2006 | Adams et al. |
| 7,177,684 B1 | 2/2007 | Kroll et al. |
| 7,181,505 B2 | 2/2007 | Haller et al. |
| D546,440 S | 7/2007 | Burnside |
| D556,153 S | 11/2007 | Burnside |
| 7,324,949 B2 | 1/2008 | Bristol |
| 7,347,843 B2 | 3/2008 | Adams et al. |
| 7,351,233 B2 | 4/2008 | Parks |
| D574,950 S | 8/2008 | Zawacki et al. |
| 7,445,614 B2 | 11/2008 | Bunodiere et al. |
| 7,479,107 B2 | 1/2009 | Zhu et al. |
| 7,713,251 B2 | 5/2010 | Tallarida et al. |
| 7,831,301 B2 | 7/2010 | Byrum |
| 7,775,966 B2 | 8/2010 | Dlugos et al. |
| 7,785,302 B2 | 8/2010 | Powers |
| 7,844,341 B2 | 11/2010 | Von Arx et al. |
| 7,909,769 B2 | 3/2011 | Zhu et al. |
| 7,909,804 B2 | 3/2011 | Stats |
| 7,942,863 B2 | 5/2011 | Kalpin et al. |
| 7,947,022 B2 | 5/2011 | Amin et al. |
| 7,959,615 B2 | 6/2011 | Stats et al. |
| 7,972,314 B2 | 7/2011 | Bizup et al. |
| 8,025,639 B2 | 9/2011 | Powers et al. |
| 8,029,482 B2 | 10/2011 | Maniar et al. |
| 8,092,435 B2 | 1/2012 | Beling et al. |
| 8,140,160 B2 | 3/2012 | Pless et al. |
| 8,147,455 B2 | 4/2012 | Butts et al. |
| 8,175,694 B2 | 5/2012 | Webb et al. |
| 8,177,762 B2 | 5/2012 | Beasley et al. |
| 8,202,259 B2 | 6/2012 | Evans et al. |
| 8,301,254 B2 | 10/2012 | Mosesov et al. |
| D676,955 S | 2/2013 | Orome |
| 8,382,724 B2 | 2/2013 | Maniar et al. |
| 8,391,981 B2 | 3/2013 | Mosesov |
| 8,396,803 B1 | 3/2013 | Dala et al. |
| 8,401,659 B2 | 3/2013 | Von Arx et al. |
| 8,409,221 B2 | 4/2013 | Franklin et al. |
| 8,439,835 B1 * | 5/2013 | McKinley ............ A61B 5/0205 600/301 |
| 8,475,417 B2 | 7/2013 | Powers et al. |
| 8,491,547 B2 | 7/2013 | Olsen et al. |
| 8,535,280 B2 | 9/2013 | Mitchell et al. |
| 8,535,281 B2 | 9/2013 | Travis et al. |
| 8,545,460 B2 | 10/2013 | Beasley et al. |
| 8,608,713 B2 | 12/2013 | Beasley et al. |
| 8,608,727 B2 | 12/2013 | Michels et al. |
| 8,615,305 B2 | 12/2013 | Von Arx et al. |
| 8,641,676 B2 | 2/2014 | Butts et al. |
| 8,641,688 B2 | 2/2014 | Powers et al. |
| 8,660,659 B2 | 2/2014 | Mosesov et al. |
| 8,744,581 B2 | 6/2014 | Mosesov |
| 8,805,478 B2 | 8/2014 | Powers et al. |
| 8,827,904 B2 | 9/2014 | Ball et al. |
| 8,920,389 B2 | 12/2014 | Kalpin et al. |
| 8,920,390 B2 | 12/2014 | Dalton et al. |
| 8,926,573 B2 | 1/2015 | Smith et al. |
| 8,932,271 B2 | 1/2015 | Hamatake et al. |
| 8,939,947 B2 | 1/2015 | Maniar et al. |
| 9,011,388 B2 | 4/2015 | Schwartz et al. |
| 9,017,256 B2 | 4/2015 | Gottesman |
| 9,072,881 B2 | 7/2015 | Dalton et al. |
| 9,079,004 B2 | 7/2015 | Wiley et al. |
| 9,101,264 B2 | 8/2015 | Acquista |
| 9,186,455 B2 | 11/2015 | Moyer |
| D748,249 S | 1/2016 | Pittet et al. |
| 9,248,268 B2 | 2/2016 | Wiley et al. |
| 9,327,106 B2 | 5/2016 | Beling et al. |
| 9,358,378 B2 | 6/2016 | Hanson et al. |
| 9,421,352 B2 | 8/2016 | Butts et al. |
| 9,474,888 B2 | 10/2016 | Wiley et al. |
| 9,485,883 B2 | 11/2016 | Koyama |
| 9,498,130 B2 | 11/2016 | Najafi et al. |
| 9,579,496 B2 | 2/2017 | Evans et al. |
| 9,603,992 B2 | 3/2017 | Powers |
| 9,603,993 B2 | 3/2017 | Powers |
| 9,642,556 B2 | 5/2017 | Mo et al. |
| 9,681,825 B2 | 6/2017 | Acquista |
| 9,717,895 B2 | 8/2017 | Wiley et al. |
| 9,814,833 B2 | 11/2017 | Kalpin |
| 9,821,150 B2 | 11/2017 | Pamment |
| 9,937,337 B2 | 4/2018 | Powers et al. |
| 9,950,150 B2 | 4/2018 | Beling et al. |
| 10,016,585 B2 | 7/2018 | Powers et al. |
| 10,022,094 B2 | 7/2018 | Kerr et al. |
| 10,052,470 B2 | 8/2018 | Powers et al. |
| 10,052,471 B2 | 8/2018 | Hamatake et al. |
| 10,086,186 B2 | 10/2018 | Evans et al. |
| 10,155,101 B2 | 12/2018 | Wiley et al. |
| 10,207,095 B2 | 2/2019 | Barron et al. |
| 10,307,581 B2 | 6/2019 | Hibdon et al. |
| 10,321,292 B2 | 6/2019 | Pflugh et al. |
| 2001/0027331 A1 | 10/2001 | Thompson |
| 2002/0052539 A1 | 5/2002 | Haller et al. |
| 2002/0193846 A1 | 12/2002 | Pool et al. |
| 2003/0014091 A1 | 1/2003 | Rastegar et al. |
| 2004/0054352 A1 * | 3/2004 | Adams ................ A61B 5/0028 604/891.1 |
| 2005/0124980 A1 | 6/2005 | Sanders |
| 2006/0116648 A1 | 6/2006 | Hamatake |
| 2006/0178617 A1 | 8/2006 | Adams et al. |
| 2006/0178648 A1 | 8/2006 | Barron et al. |
| 2007/0016089 A1 | 1/2007 | Fischell et al. |
| 2007/0078391 A1 | 4/2007 | Wortley et al. |
| 2007/0135765 A1 | 6/2007 | Miller et al. |
| 2007/0270672 A1 | 11/2007 | Hayter |
| 2008/0114308 A1 * | 5/2008 | di Palma ........... A61M 39/0208 604/246 |
| 2009/0118683 A1 | 5/2009 | Hanson et al. |
| 2009/0227951 A1 | 9/2009 | Powers et al. |
| 2010/0191166 A1 | 7/2010 | Phillips et al. |
| 2010/0274221 A1 | 10/2010 | Sigg et al. |
| 2011/0184342 A1 | 7/2011 | Pesach et al. |
| 2012/0172711 A1 | 7/2012 | Kerr et al. |

(56) References Cited

U.S. PATENT DOCUMENTS

| | | | |
|---|---|---|---|
| 2012/0245439 A1* | 9/2012 | Andre | A61B 5/0205 600/310 |
| 2013/0150811 A1 | 6/2013 | Horgan | |
| 2014/0088519 A1 | 3/2014 | Kerr | |
| 2014/0207086 A1 | 7/2014 | Stats et al. | |
| 2014/0236105 A1 | 8/2014 | Hanson et al. | |
| 2014/0249503 A1 | 9/2014 | Bennett et al. | |
| 2015/0025478 A1 | 1/2015 | Hibdon et al. | |
| 2015/0112315 A1 | 4/2015 | Cudak et al. | |
| 2016/0317797 A1 | 11/2016 | Smith et al. | |
| 2017/0028185 A1 | 2/2017 | Wiley et al. | |
| 2017/0340872 A1 | 11/2017 | Hanson et al. | |
| 2018/0043149 A1 | 2/2018 | Martin | |
| 2018/0078751 A1 | 3/2018 | Fedor et al. | |
| 2018/0147343 A1 | 5/2018 | Tyson | |
| 2018/0161565 A1 | 6/2018 | Maniar et al. | |
| 2018/0177982 A1 | 6/2018 | Albany et al. | |
| 2018/0193626 A1 | 7/2018 | Beling et al. | |
| 2019/0054284 A1 | 2/2019 | Smith et al. | |
| 2020/0179669 A1 | 6/2020 | Mitchell et al. | |

FOREIGN PATENT DOCUMENTS

| | | | |
|---|---|---|---|
| DE | 102011078711 A1 | 1/2013 | |
| EP | 0392199 A1 | 10/1990 | |
| EP | 1391218 A3 | 4/2004 | |
| EP | 1413329 B1 | 12/2005 | |
| EP | 1773448 A1 | 4/2007 | |
| EP | 1962921 A2 | 9/2008 | |
| EP | 2020945 B1 | 2/2013 | |
| EP | 2859911 A1 | 4/2015 | |
| EP | 1874393 B1 | 9/2017 | |
| EP | 2416828 B1 | 2/2018 | |
| EP | 2501294 B1 | 8/2018 | |
| ES | 2041000 T3 | 11/1993 | |
| ES | 2041461 T3 | 11/1993 | |
| ES | 2136613 T3 | 12/1999 | |
| JP | 2000513952 A | 10/2000 | |
| JP | 4795523 B2 | 11/2000 | |
| JP | 2005169113 A | 6/2005 | |
| JP | 4947876 B2 | 3/2012 | |
| JP | 2016504158 A | 2/2016 | |
| WO | 9934859 A1 | 7/1999 | |
| WO | 2010118144 A1 | 10/2010 | |
| WO | 2015097255 A2 | 7/2015 | |
| WO | 2019118929 A1 | 6/2019 | |
| WO | 2020106804 A1 | 5/2020 | |
| WO | 2020106842 A1 | 5/2020 | |
| WO | 2020106890 A1 | 5/2020 | |

OTHER PUBLICATIONS

International Search Report and Written Opinion dated Feb. 18, 2020; International Application No. PCT/US2019/062416; 14 pages.
International Search Report and Written Opinion dated Feb. 18, 2020; International Application No. PCT/US2019/062483; 12 pages.
International Search Report and Written Opinion dated Feb. 24, 2020; International Application No. PCT/US2019/062350; 14 pages.
Kuo et al., "Blockcain distributed ledger technologies for biomedical and health care applications", Journal of the American Medical Informatics Association, vol. 24, No. 6, Sep. 8, 2017, pp. 1211-1220.
International Search Report and Written Opinion dated Mar. 31, 2021; International Application No. PCT/US20/70803; 16 pages.

* cited by examiner

VASCULAR ACCESS DEVICES, SYSTEMS, AND METHODS FOR MONITORING PATIENT HEALTH

TECHNICAL FIELD

The present technology is generally directed to vascular access devices and associated systems and methods of use. In particular, the present technology is directed to vascular access devices and associated systems and methods for monitoring patient health.

BACKGROUND

Anticancer treatments have brought about definite advances in patient survival rates. However, treatment is associated with significant toxicity that is potentially life-threatening, and can often result in poor treatment adherence, impaired quality of life, and mortality. Systematic monitoring of the patient's health during chemotherapy treatment is therefore crucial to early detection of life-threatening health conditions. One conventional approach to monitoring patient health is soliciting feedback from the patient at regular intervals (for example, when the patient comes in for treatment) using standardized patient-reported outcome ("PRO") questionnaires. However, because of the delay from onset to the reporting of symptoms, the information received on PRO questionnaires can have limited diagnostic value, as the time to treat may have passed, or the patient may have inaccurately reported their symptoms or forgotten to report some symptoms altogether. Systematic web-based collection of patient-reported symptoms has shown better results, with recent studies demonstrating that cancer patients assigned to electronic, patient-reported symptom monitoring during routine chemotherapy have a 20% increased survival rate as compared to patients undergoing usual care (i.e., without an obligation to self-report). (Basch et al., *Overall Survival Results of a Trial Assessing Patient-Reported Outcomes for Symptom Monitoring During Routine Cancer Treatment*, JAMA, Jul. 11, 2017, Vol. 318, No. 2.) However, system alerts based mostly or entirely on PRO's can lead to unnecessary emergency room visits and hospital admissions, which unnecessarily puts the patient at an increased risk of infection, great stress, and drives up patient costs. Accordingly, there is a need for improved systems for monitoring patient health.

SUMMARY

The vascular access devices, systems, and methods of the present technology are configured to obtain patient physiological data while the vascular access device is implanted within the patient, and determine one or more physiological parameters based on the measurements. The system may determine certain physiological parameters, for example, that indicate one or more symptoms of a health condition that requires immediate medical attention or hospitalization. Such physiological parameters can include those related to temperature, patient movement/activity level, heart rate, respiratory rate, blood oxygen saturation, and/or other suitable parameters described herein. Based on these parameters, the system may provide an indication to the patient and/or clinician that the patient has contracted or is at risk of contracting an adverse health condition. The system of the present technology may be especially beneficial for cancer patients undergoing chemotherapy, as chemotherapy comes with many side effects that could be fatal to the patient if not treated immediately. Therefore, early detection of known symptoms is crucial to patient quality of life and survival.

The subject technology is illustrated, for example, according to various aspects described below, including with reference to FIGS. 1-9. Various examples of aspects of the subject technology are described as numbered clauses (1, 2, 3, etc.) for convenience. These are provided as examples and do not limit the subject technology.

1. A system for monitoring the health of a patient, the system comprising:
   a housing configured to be implanted within a human patient, the housing containing a reservoir;
   a septum adjacent the reservoir and configured to receive a needle therethrough for delivery of a fluid to the reservoir;
   a sensing element coupled to the housing and configured to obtain physiological measurements; and
   at least one controller configured to be communicatively coupled to the sensing element, wherein the at least one controller is further configured to:
   obtain the physiological measurements via the sensing element while the housing is implanted within the patient;
   determine at least one physiological parameter based on the physiological measurements;
   compare the at least one physiological parameter to a predetermined threshold; and
   based on the comparison, provide an indication of the patient's health.

2. The system of Clause 1, wherein the sensing element comprises at least one of a temperature sensing element, a heart rate sensing element, a respiratory rate sensing element, a movement sensing element, a pressure sensing element, an electrical signal sensing element, and an electro-optical sensing element.

3. The system of Clause 1 or Clause 2, wherein the at least one controller is configured to provide an indication that the patient is septic based on the comparison.

4. The system of any one of Clauses 1 to 3, wherein the at least one physiological parameter is at least one of a temperature parameter, a heart rate parameter, a respiratory rate parameter, and an activity level parameter.

5. The system of any one of Clauses 1 to 4, wherein the at least one physiological parameter is at least two of a temperature parameter, a heart rate parameter, a respiratory rate parameter, and an activity level parameter.

6. The system of any one of Clauses 1 to 5, wherein:
   the at least one physiological parameter comprises at least two of a temperature parameter, a heart rate parameter, a respiratory rate parameter, and an activity level parameter;
   comparing the at least two physiological parameters to the predetermined threshold includes comparing each of the at least two physiological parameters to a corresponding predetermined threshold.

7. The system of any one of Clauses 1 to 5, wherein:
   the at least one physiological parameter comprises at least three of a temperature parameter,
   a heart rate parameter, a respiratory rate parameter, and an activity level parameter;
   comparing the at least three physiological parameters to the predetermined threshold includes comparing each of the at least three physiological parameters to a corresponding predetermined threshold.

8. The system of any one of Clauses 1 to 5, wherein:
   the at least one physiological parameter comprises a temperature parameter, a heart rate parameter, a respiratory rate parameter, and an activity level parameter;
   comparing the at least one physiological parameter to the predetermined threshold includes comparing the temperature parameter, the heart rate parameter, the respiratory rate parameter, and the activity level parameter to a predetermined temperature rate threshold, a predetermined heart rate threshold, a predetermined respiratory rate threshold, and a predetermined activity level threshold, respectively.
9. The system of any one of Clauses 1 to 8, wherein the at least one controller is configured to determine at least one of a blood pH less than 7.2, a serum lactate greater than 2 mmol/L, a serum lactate greater than 4 mmol/L, a blood procalcitonin level above 2 ng/mL, and a low central venous pressure less than 2 mm/Hg.
10. The system of any one of Clauses 1 to 9, wherein the sensing element is configured to obtain at least some of the physiological measurements continuously.
11. The system of any one of Clauses 1 to 9, wherein the sensing element is configured to obtain at least some of the physiological measurements periodically.
12. The system of any one of Clauses 1 to 11, wherein the at least one controller is configured to obtain at least some of the physiological measurements continuously.
13. The system of any one of Clauses 1 to 11, wherein the at least one controller is configured to obtain at least some of the physiological measurements periodically.
14. The system of any one of Clauses 1 to 13, wherein the at least one controller is configured to determine the at least one physiological parameter continuously.
15. The system of any one of Clauses 1 to 13, wherein the at least one controller is configured to determine the at least one physiological parameter periodically.
16. The system of any one of Clauses 1 to 15, wherein:
   the sensing element is configured to measure temperature;
   the at least one physiological parameter includes a temperature parameter; and
   the at least one controller is configured to:
     compare the temperature parameter to a predetermined temperature threshold;
     determine the temperature parameter is outside of the predetermined temperature threshold; and
     based on the determination, indicate that the patient is septic.
17. The system of any one of Clauses 1 to 16, wherein the temperature parameter is a body temperature of the patient, and wherein determining the temperature parameter is outside of the predetermined temperature threshold includes determining the body temperature is outside of 96-100° F.
18. The system of any one of Clauses 1 to 17, wherein the temperature parameter is a body temperature of the patient, and wherein determining the temperature parameter is outside of the predetermined temperature threshold includes determining the body temperature is outside of 96-100° F. for a predetermined amount of time.
19. The system of any one of Clauses 1 to 18, wherein the temperature parameter is a body temperature of the patient, and wherein determining the temperature parameter is outside of the predetermined temperature threshold includes determining the body temperature is greater than 100° F.
20. The system of any one of Clauses 1 to 19, wherein the temperature parameter is a body temperature of the patient, and wherein determining the temperature parameter is outside of the predetermined temperature threshold includes determining the body temperature is greater than 100° F. for a predetermined amount of time.
21. The system of any one of Clauses 1 to 20, wherein the temperature parameter is a body temperature of the patient, and wherein determining the temperature parameter is outside of the predetermined temperature threshold includes determining the body temperature is less than 96° F.
22. The system of any one of Clauses 1 to 21, wherein the temperature parameter is a body temperature of the patient, and wherein determining the temperature parameter is outside of the predetermined temperature threshold includes determining the body temperature is less than 96° F. for a predetermined amount of time.
23. The system of any one of Clauses 1 to 22, wherein the temperature parameter is a change in a body temperature, and wherein determining the temperature parameter is outside of the predetermined temperature threshold includes determining at least a 2% change in body temperature from a baseline temperature.
24. The system of any one of Clauses 1 to 23, wherein the temperature parameter is a change in a body temperature, and wherein determining the temperature parameter is outside of the predetermined temperature threshold includes determining at least a 2% change in body temperature from a baseline temperature over a predetermined amount of time.
25. The system of any one of Clauses 1 to 24, wherein the at least one physiological parameter is a temperature parameter and a heart rate parameter.
26. The system of any one of Clauses 1 to 25, wherein:
   the sensing element comprises a first sensing element configured to measure temperature and a second sensing element configured to measure heart rate;
   the at least one physiological parameter includes a temperature parameter and a heart rate parameter; and
   the at least one controller is configured to:
     compare the temperature parameter to a predetermined temperature threshold;
     compare the heart rate parameter to a predetermined heart rate threshold;
     determine the temperature parameter is outside of the predetermined temperature threshold;
     determine the heart rate parameter is outside of the predetermined heart rate threshold; and
     based on the determinations that the temperature parameter and the heart rate parameter are outside of the predetermined temperature threshold and the predetermined heart rate threshold, respectively, indicate that the patient is septic.
27. The system of any one of Clauses 1 to 26, wherein the second sensing element comprises a pulse oximeter.
28. The system of any one of Clauses 1 to 27, wherein the heart rate parameter is a heart rate of the patient, and wherein determining the heart rate parameter is outside of the predetermined threshold includes determining the heart rate of the patient is greater than 90 beats per minute.
29. The system of any one of Clauses 1 to 28, wherein the heart rate parameter is a heart rate of the patient, and wherein determining the heart rate parameter is outside of the predetermined threshold includes determining the heart rate of the patient is greater than 90 beats per minute for a predetermined amount of time.
30. The system of any one of Clauses 1 to 29, wherein the heart rate parameter is a change in a heart rate of the patient, and wherein determining the heart rate parameter is outside of the predetermined threshold includes determining the heart rate of the patient increases at least 10% from a reference heart rate of the patient.
31. The system of any one of Clauses 1 to 30, wherein the heart rate parameter is a change in the patient's heart rate, and wherein determining the heart rate parameter is outside of the predetermined threshold includes determining the heart rate of the patient increases at least 10% from a reference heart rate of the patient over a predetermined amount of time.
32. The system of any one of Clauses 1 to 31, wherein the at least one physiological parameter is a temperature parameter and a respiratory rate parameter.
33. The system of any one of Clauses 1 to 32, wherein:
the sensing element comprises a first sensing element configured to measure temperature and a second sensing element configured to measure respiratory rate;
the at least one physiological parameter includes a temperature parameter and a respiratory rate parameter; and
the at least one controller is configured to:
compare the temperature parameter to a predetermined temperature threshold;
compare the respiratory rate parameter to a predetermined respiratory rate threshold;
determine the temperature parameter is outside of the predetermined temperature threshold;
determine the respiratory rate parameter is outside of the predetermined respiratory rate threshold; and
based on the determinations that the temperature parameter and the respiratory rate parameter are outside of the predetermined temperature threshold and the predetermined respiratory rate threshold, respectively, indicate that the patient is septic.
34. The system of Clause 32 or Clause 33, wherein the respiratory rate parameter is a respiratory rate of the patient, and wherein determining the respiratory rate parameter is outside of the predetermined threshold includes determining the respiratory rate of the patient is greater than 15 breaths per minute.
35. The system of any one of Clauses 32 to 34, wherein the respiratory rate parameter is a respiratory rate of the patient, and wherein determining the respiratory rate parameter is outside of the predetermined threshold includes determining the respiratory rate of the patient is greater than 15 breaths per minute for a predetermined amount of time.
36. The system of any one of Clauses 1 to 35, wherein the at least one physiological parameter is a temperature parameter and an activity level parameter.
37. The system of any one of Clauses 1 to 35, wherein:
the sensing element comprises a first sensing element configured to measure temperature and a second sensing element configured to measure movement of the patient;
the at least one physiological parameter includes a temperature parameter and an activity level parameter; and
the at least one controller is configured to:
compare the temperature parameter to a predetermined temperature threshold;
compare the activity level parameter to a predetermined activity level threshold;
determine the temperature parameter is outside of the predetermined temperature threshold;
determine the activity level parameter is outside of the predetermined activity level threshold; and
based on the determinations that the temperature parameter and the activity level parameter are outside of the predetermined temperature threshold and the predetermined activity level threshold, respectively, indicate that the patient is septic.
38. The system of Clause 36 or Clause 37, wherein the second sensing element comprises an accelerometer.
39. The system of any one of Clauses 36 to 38, wherein the activity level parameter is an amount of movement of the patient over a predetermined amount of time, and wherein determining the activity level parameter is outside of the predetermined threshold includes determining the amount of movement of the patient is less than the predetermined threshold over the predetermined amount of time.
40a. The system of Clause 39, wherein the predetermined threshold is based at least in part on a baseline activity level of the patient and/or an age-adjusted expected activity level.
40b. The system of any one of Clauses 37 to 40a, wherein the activity level parameter is an amount of movement of the patient over a predetermined amount of time, and wherein determining the activity level parameter is outside of the predetermined threshold includes determining the amount of movement of the patient is less than 20% of a baseline activity level of the patient.
41. The system of any one of Clauses 1 to 40, wherein the at least one controller is integrated with the housing.
42. The system of any one of Clauses 1 to 41, wherein the at least one controller is further configured to transmit the physiological measurements and/or the at least one physiological parameter to one or more remote computing devices.
43. The system of any one of Clauses 1 to 42, wherein:
the at least one controller comprises a first controller and a second controller;
the first controller is integrated with the housing and the second controller is separate from the housing and not configured to be implanted within the patient; and
the first controller is in wireless communication with the second controller.
44. The system of Clause 43, wherein the first controller communicates with the second controller over at least one of a local area network and/or a personal area network.
45. The system of Clause 43, wherein the first controller communicates with the second controller via Bluetooth.
46. The system of Clause 43, wherein the first controller is remote from the second controller and communicates with the second controller via a wide area network.
47. The system of any one of Clauses 43 to 46, wherein the second controller is a smart device.
48. The system of any one of Clauses 1 to 42, wherein:
the at least one controller comprises a first controller, a second controller, and a third controller;
the first controller is integrated with the housing;
the second controller is separate from the housing and communicates with the first controller via a local area network and/or a personal area network;
the third controller is separate from the housing and is one or more remote computing devices.

49. The system of any one of Clauses 1 to 48, further comprising a catheter extending from the housing, the catheter having (a) a proximal end coupled to the housing and in fluid communication with the reservoir, and (b) a distal end configured to be positioned within a blood vessel of a patient.
50. The system of Clause 49, wherein the sensing element is positioned at or near the distal end of the catheter and/or the reservoir.
51. The system of Clause 49, wherein the sensing element is a first sensing element and the system includes a second sensing element positioned at or near the distal end of the catheter and/or the reservoir, wherein the second sensing element is communicatively coupled to the at least one controller.
52. The system of any one of Clauses 1 to 51, wherein the sensing element is integrated with the housing.
53. The system of any one of Clauses 1 to 52, wherein at least a portion of the sensing element is positioned at an exterior surface of the housing.
54. The system of any one of Clauses 1 to 53, wherein: the sensing element comprises a pulse oximeter configured to emit light; the housing includes a window and the sensing element is positioned adjacent the window, wherein the window is configured to allow the light emitted from the pulse oximeter to pass through to a location external to the housing.
55. The system of Clause 54, wherein the window is configured to allow reflected light to pass back through.
56. The system of Clause 54 or Clause 55 wherein the window comprises sapphire.
57. The system of any one of Clauses 54 to 56, wherein the window is brazed to the housing.
58. The system of any one of Clauses 1 to 57, wherein, based on the comparison, the controller is configured to provide an indication of a health condition of a patient, the health condition being at least one of sepsis, pulmonary embolism, metastatic spinal cord compression, anemia, dehydration/volume depletion, vomiting, pneumonia, congestive heart failure, performance status, arrythmia, neutropenic fever, acute myocardial infarction, pain, opioid toxicity, hyperglycemic/diabetic ketoacidosis, hypoglycemia, hyperkalemia, hypercalcemia, hyponatremia, one or more brain metastases, superior vena cava syndrome, gastrointestinal hemorrhage, immunotherapy-induced or radiation pneumonitis, immunotherapy-induced colitis, diarrhea, cerebrovascular accident, stroke, pathological fracture, hemoptysis, hematemesis, medication-induced QT prolongation, heart block, tumor lysis syndrome, sickle cell anemia crisis, gastroparesis/cyclic vomiting syndrome, hemophilia, cystic fibrosis, chronic pain, and seizure.
59. A system for monitoring the health of a patient, the system comprising:
a housing configured to be implanted within a human patient, the housing containing a reservoir;
a septum adjacent the reservoir and configured to receive a needle therethrough for delivery of a fluid to the reservoir;
a sensing element coupled to the housing and configured to obtain physiological measurements; and
at least one controller configured to be communicatively coupled to the sensing element,
wherein the at least one controller is further configured to:
obtain the physiological measurements via the sensing element while the housing is implanted within the patient;
determine at least one physiological parameter based on the physiological measurements, wherein the at least one physiological parameter includes a temperature parameter and at least one of a heart rate parameter, a respiratory rate parameter, and an activity level parameter;
compare the at least one physiological parameter to a predetermined threshold, including comparing the temperature parameter to a predetermined temperature threshold and comparing the at least one of the heart rate parameter, the respiratory rate parameter, and the activity level parameter to a predetermined heart rate threshold, a predetermined temperature threshold, and a predetermined activity level threshold, respectively; and
based on the comparison, provide an indication that the patient is septic.
60. The system of Clause 59, wherein the sensing element comprises at least one of a temperature sensing element, a heart rate sensing element, a respiratory rate sensing element, a movement sensing element, a pressure sensing element, an electrical signal sensing element, and an electro-optical sensing element.
61. The system of Clause 59 or Clause 60, wherein the temperature parameter is a body temperature of the patient, and wherein determining the temperature parameter is outside of the predetermined temperature threshold includes determining the body temperature is outside of 96-100° F.
62. The system of any one of Clauses 59 to 61, wherein the temperature parameter is a body temperature of the patient, and wherein determining the temperature parameter is outside of the predetermined temperature threshold includes determining the body temperature is greater than 100° F. or determining the body temperature is less than 96° F.
63. The system of any one of Clauses 59 to 62, wherein the sensing element comprises at least one of a pulse oximeter and an electrode.
64. The system of any one of Clauses 59 to 63, wherein the heart rate parameter is a heart rate of the patient, and wherein determining the heart rate parameter is outside of the predetermined heart rate threshold includes determining the heart rate of the patient is greater than 90 beats per minute.
65. The system of any one of Clauses 59 to 64, wherein the heart rate parameter is a change in a heart rate of the patient, and wherein determining the heart rate parameter is outside of the predetermined heart rate threshold includes determining the heart rate of the patient increases at least 10% from a reference heart rate of the patient.
66. The system of any one of Clauses 59 to 65, wherein the respiratory rate parameter is a respiratory rate of the patient, and wherein determining the respiratory rate parameter is outside of the predetermined respiratory rate threshold includes determining the respiratory rate of the patient is greater than 15 breaths per minute.
67. The system of any one of Clauses 59 to 66, wherein the sensing element comprises an accelerometer.
68. The system of any one of Clauses 59 to 67, wherein the activity level parameter is an amount of movement of the patient over a predetermined amount of time, and wherein determining the activity level parameter is outside of the predetermined threshold includes determining the amount of movement of the patient is less than the predetermined threshold over the predetermined amount of time.

69. The system of Clause 68, wherein the predetermined threshold is based at least in part on a baseline activity level of the patient.

70. A system for monitoring the health of a patient, the system comprising:
a housing configured to be implanted within a human patient, the housing containing a reservoir;
a septum adjacent the reservoir and configured to receive a needle therethrough for delivery of a fluid to the reservoir;
a sensing element coupled to the housing and configured to obtain physiological measurements, the sensing element including a pulse oximeter configured to emit light;
at least one controller configured to be communicatively coupled to the sensing element, wherein the at least one controller is further configured to:
obtain the physiological measurements via the sensing element while the housing is implanted within the patient;
determine at least one physiological parameter based on the physiological measurements, wherein the at least one physiological parameter includes a temperature parameter and at least one of a heart rate parameter, a respiratory rate parameter, and an activity level parameter;
compare the at least one physiological parameter to a predetermined threshold, including comparing the temperature parameter to a predetermined temperature threshold and comparing the at least one of the heart rate parameter, the respiratory rate parameter, and the activity level parameter to a predetermined heart rate threshold, a predetermined temperature threshold, and a predetermined activity level threshold, respectively; and
based on the comparison, provide an indication that the patient is septic.

71. The system of Clause 70, wherein the sensing element is integrated with the housing.

72. The system of Clause 70 or Clause 71, wherein the housing includes a window and the sensing element is positioned adjacent the window, wherein the window is configured to (a) allow the light emitted from the pulse oximeter to pass through to a location external to the housing, and (b) all a reflection of the light to pass back through the window.

73. The system of any one of Clauses 70 to 72, wherein the sensing element further comprises at least one of an accelerometer and an electrode.

74. The system of any one of Clauses 70 to 73, wherein the at least one physiological parameter is the temperature parameter and the heart rate parameter, and wherein:
the temperature parameter is a body temperature of the patient and determining the temperature parameter is outside of the predetermined temperature threshold includes determining the body temperature is outside of 96-100° F.; and
the heart rate parameter is a change in a heart rate of the patient, and wherein determining the heart rate parameter is outside of the predetermined heart rate threshold includes determining the heart rate of the patient increases at least 10% from a reference heart rate of the patient.

75. A system for monitoring the health of a patient, the system comprising:
a housing configured to be implanted within a human patient, the housing containing a reservoir;
a septum adjacent the reservoir and configured to receive a needle therethrough for delivery of a fluid to the reservoir;
a sensing element coupled to the housing and configured to obtain physiological measurements;
a catheter extending from the housing, the catheter having (a) a proximal end coupled to the housing and in fluid communication with the reservoir, and (b) a distal end configured to be positioned within a blood vessel of a patient; and
at least one controller configured to be communicatively coupled to the sensing element, wherein the at least one controller is further configured to:
obtain the physiological measurements via the sensing element while the housing is implanted within the patient;
determine at least one physiological parameter based on the physiological measurements, wherein the at least one physiological parameter includes a temperature parameter and at least one of a heart rate parameter, a respiratory rate parameter, and an activity level parameter;
compare the at least one physiological parameter to a predetermined threshold, including comparing the temperature parameter to a predetermined temperature threshold and the at least one of the heart rate parameter, the respiratory rate parameter, and the activity level parameter to a predetermined heart rate threshold, a predetermined temperature threshold, and a predetermined activity level threshold, respectively; and
based on the comparison, provide an indication that the patient is septic.

76. The system of Clause 75, wherein the sensing element comprises (a) a sensor configured to measure temperature and (b) at least one of an accelerometer and an electrode.

77. The system of Clause 75 or Clause 76, wherein the sensing element comprises (a) a sensor configured to measure temperature and (b) a pulse oximeter.

78. The system of any one of Clauses 75 to 77, wherein the at least one physiological parameter is the temperature parameter and the heart rate parameter, and wherein:
the temperature parameter is a body temperature of the patient and determining the temperature parameter is outside of the predetermined temperature threshold includes determining the body temperature is outside of 96-100° F.; and
the heart rate parameter is a change in a heart rate of the patient, and wherein determining the heart rate parameter is outside of the predetermined heart rate threshold includes determining the heart rate of the patient increases at least 10% from a reference heart rate of the patient.

79. A method for monitoring the health of a patient, the method comprising:
obtaining physiological measurements of the patient via a sensing element coupled to a vascular access device while the vascular access device is implanted within the patient, the vascular access device further comprising a housing containing a reservoir and a septum adjacent the reservoir and configured to receive a needle therethrough for delivery of a fluid to the reservoir;

determining at least one physiological parameter based on the physiological measurements;

comparing the at least one physiological parameter to a predetermined threshold; and based on the comparison, providing an indication of the patient's health.

80. The method of Clause 79, wherein the sensing element comprises at least one of a temperature sensing element, a heart rate sensing element, a respiratory rate sensing element, a movement sensing element, a pressure sensing element, and an electrical signal sensing element.

81. The method of Clause 79 or Clause 80, wherein the at least one controller is configured to provide an indication that the patient is septic based on the comparison.

82. The method of any one of Clauses 79 to 81, wherein the at least one physiological parameter is at least one of a temperature parameter, a heart rate parameter, a respiratory rate parameter, and an activity level parameter.

83. The method of any one of Clauses 79 to 82, wherein the at least one physiological parameter is at least two of a temperature parameter, a heart rate parameter, a respiratory rate parameter, and an activity level parameter.

84. The method of any one of Clauses 79 to 83, wherein:
the at least one physiological parameter comprises at least two of a temperature parameter, a heart rate parameter, a respiratory rate parameter, and an activity level parameter;
comparing the at least two physiological parameters to the predetermined threshold includes comparing each of the at least two physiological parameters to a corresponding predetermined threshold.

85. The method of any one of Clauses 79 to 84, wherein:
the at least one physiological parameter comprises at least three of a temperature parameter, a heart rate parameter, a respiratory rate parameter, and an activity level parameter;
comparing the at least three physiological parameters to the predetermined threshold includes comparing each of the at least three physiological parameters to a corresponding predetermined threshold.

86. The method of any one of Clauses 79 to 85, wherein:
the at least one physiological parameter comprises a temperature parameter, a heart rate parameter, a respiratory rate parameter, and an activity level parameter;
comparing the at least one physiological parameter to the predetermined threshold includes comparing the temperature parameter, the heart rate parameter, the respiratory rate parameter, and the activity level parameter to a predetermined temperature rate threshold, a predetermined heart rate threshold, a predetermined respiratory rate threshold, and a predetermined activity level threshold, respectively.

87. The method of any one of Clauses 79 to 86, wherein the at least one controller is configured to determine at least one of a blood pH less than 7.2, a serum lactate greater than 2 mmol/L, a serum lactate greater than 4 mmol/L, a blood procalcitonin level above 2 ng/mL, and a low central venous pressure less than 2 mm/Hg.

88. The method of any one of Clauses 79 to 87, wherein the sensing element is configured to obtain at least some of the physiological measurements continuously.

89. The method of any one of Clauses 79 to 87, wherein the sensing element is configured to obtain at least some of the physiological measurements periodically.

90. The method of any one of Clauses 79 to 89, wherein the at least one controller is configured to obtain at least some of the physiological measurements continuously.

91. The method of any one of Clauses 79 to 89, wherein the at least one controller is configured to obtain at least some of the physiological measurements periodically.

92. The method of any one of Clauses 79 to 91, wherein the at least one controller is configured to determine the at least one physiological parameter continuously.

93. The method of any one of Clauses 79 to 92, wherein the at least one controller is configured to determine the at least one physiological parameter periodically.

94. The method of any one of Clauses 79 to 93, wherein:
the sensing element is configured to measure temperature;
the at least one physiological parameter includes a temperature parameter; and
the at least one controller is configured to:
compare the temperature parameter to a predetermined temperature threshold;
determine the temperature parameter is outside of the predetermined temperature threshold; and
based on the determination, indicate that the patient is septic.

95. The method of any one of Clauses 79 to 94, wherein the temperature parameter is a body temperature of the patient, and wherein determining the temperature parameter is outside of the predetermined temperature threshold includes determining the body temperature is outside of 96-100° F.

96. The method of any one of Clauses 79 to 95, wherein the temperature parameter is a body temperature of the patient, and wherein determining the temperature parameter is outside of the predetermined temperature threshold includes determining the body temperature is outside of 96-100° F. for a predetermined amount of time.

97. The method of any one of Clauses 79 to 96, wherein the temperature parameter is a body temperature of the patient, and wherein determining the temperature parameter is outside of the predetermined temperature threshold includes determining the body temperature is greater than 100° F.

98. The method of any one of Clauses 79 to 97, wherein the temperature parameter is a body temperature of the patient, and wherein determining the temperature parameter is outside of the predetermined temperature threshold includes determining the body temperature is greater than 100° F. for a predetermined amount of time.

99. The method of any one of Clauses 79 to 98, wherein the temperature parameter is a body temperature of the patient, and wherein determining the temperature parameter is outside of the predetermined temperature threshold includes determining the body temperature is less than 96° F.

100. The method of any one of Clauses 79 to 99, wherein the temperature parameter is a body temperature of the patient, and wherein determining the temperature parameter is outside of the predetermined temperature threshold includes determining the body temperature is less than 96° F. for a predetermined amount of time.

101. The method of any one of Clauses 79 to 100, wherein the temperature parameter is a change in a body temperature, and wherein determining the temperature parameter is outside of the predetermined temperature threshold includes determining at least a 2% change in body temperature from a baseline temperature.
102. The method of any one of Clauses 79 to 101, wherein the temperature parameter is a change in a body temperature, and wherein determining the temperature parameter is outside of the predetermined temperature threshold includes determining at least a 2% change in body temperature from a baseline temperature over a predetermined amount of time.
103. The method of any one of Clauses 79 to 102, wherein the at least one physiological parameter is a temperature parameter and a heart rate parameter.
104. The method of any one of Clauses 79 to 103, wherein:
the sensing element comprises a first sensing element configured to measure temperature and a second sensing element configured to measure heart rate;
the at least one physiological parameter includes a temperature parameter and a heart rate parameter; and
the at least one controller is configured to:
compare the temperature parameter to a predetermined temperature threshold;
compare the heart rate parameter to a predetermined heart rate threshold;
determine the temperature parameter is outside of the predetermined temperature threshold;
determine the heart rate parameter is outside of the predetermined heart rate threshold; and
based on the determinations that the temperature parameter and the heart rate parameter are outside of the predetermined temperature threshold and the predetermined heart rate threshold, respectively, indicate that the patient is septic.
105. The method of any one of Clauses 79 to 104, wherein the second sensing element comprises a pulse oximeter.
106. The method of any one of Clauses 79 to 105, wherein the heart rate parameter is a heart rate of the patient, and wherein determining the heart rate parameter is outside of the predetermined threshold includes determining the heart rate of the patient is greater than 90 beats per minute.
107. The method of any one of Clauses 79 to 106, wherein the heart rate parameter is a heart rate of the patient, and wherein determining the heart rate parameter is outside of the predetermined threshold includes determining the heart rate of the patient is greater than 90 beats per minute for a predetermined amount of time.
108. The method of any one of Clauses 79 to 107, wherein the heart rate parameter is a change in a heart rate of the patient, and wherein determining the heart rate parameter is outside of the predetermined threshold includes determining the heart rate of the patient increases at least 10% from a reference heart rate of the patient.
109. The method of any one of Clauses 79 to 108, wherein the heart rate parameter is a change in the patient's heart rate, and wherein determining the heart rate parameter is outside of the predetermined threshold includes determining the heart rate of the patient increases at least 10% from a reference heart rate of the patient over a predetermined amount of time.
110. The method of any one of Clauses 79 to 109, wherein the at least one physiological parameter is a temperature parameter and a respiratory rate parameter.
111. The method of any one of Clauses 79 to 110, wherein:
the sensing element comprises a first sensing element configured to measure temperature and a second sensing element configured to measure respiratory rate;
the at least one physiological parameter includes a temperature parameter and a respiratory rate parameter; and
the at least one controller is configured to:
compare the temperature parameter to a predetermined temperature threshold;
compare the respiratory rate parameter to a predetermined respiratory rate threshold;
determine the temperature parameter is outside of the predetermined temperature threshold;
determine the respiratory rate parameter is outside of the predetermined respiratory rate threshold; and
based on the determinations that the temperature parameter and the respiratory rate parameter are outside of the predetermined temperature threshold and the predetermined respiratory rate threshold, respectively, indicate that the patient is septic.
112. The method of any one of Clauses 79 to 111, wherein the respiratory rate parameter is a respiratory rate of the patient, and wherein determining the respiratory rate parameter is outside of the predetermined threshold includes determining the respiratory rate of the patient is greater than 15 breaths per minute.
113. The method of any one of Clauses 79 to 112, wherein the respiratory rate parameter is a respiratory rate of the patient, and wherein determining the respiratory rate parameter is outside of the predetermined threshold includes determining the respiratory rate of the patient is greater than 15 breaths per minute for a predetermined amount of time.
114. The method of any one of Clauses 79 to 113, wherein the at least one physiological parameter is a temperature parameter and an activity level parameter.
115. The method of any one of Clauses 79 to 114, wherein:
the sensing element comprises a first sensing element configured to measure temperature and a second sensing element configured to measure movement of the patient;
the at least one physiological parameter includes a temperature parameter and an activity level parameter; and
the at least one controller is configured to:
compare the temperature parameter to a predetermined temperature threshold;
compare the activity level parameter to a predetermined activity level threshold;
determine the temperature parameter is outside of the predetermined temperature threshold;
determine the activity level parameter is outside of the predetermined activity level threshold; and
based on the determinations that the temperature parameter and the activity level parameter are outside of the predetermined temperature threshold and the predetermined activity level threshold, respectively, indicate that the patient is septic.
116. The method of any one of Clauses 79 to 115, wherein the second sensing element comprises an accelerometer.
117. The method of any one of Clauses 79 to 116, wherein the activity level parameter is an amount of movement of the patient over a predetermined amount of time, and wherein determining the activity level parameter is outside of the predetermined threshold includes determining the amount of movement of the patient is less than the predetermined threshold over the predetermined amount of time.

118. The method of Clause 117, wherein the predetermined threshold is based at least in part on a baseline activity level of the patient.

119. The method of any one of Clauses 79 to 118, wherein the at least one controller is integrated with the housing.

120. The method of any one of Clauses 79 to 119, wherein the at least one controller is further configured to transmit the physiological measurements and/or the at least one physiological parameter to one or more remote computing devices.

121. The method of any one of Clauses 79 to 120, wherein:
the at least one controller comprises a first controller and a second controller;
the first controller is integrated with the housing and the second controller is separate from the housing and not configured to be implanted within the patient; and
the first controller is in wireless communication with the second controller.

122. The method of Clause 121, wherein the first controller communicates with the second controller over at least one of a local area network and/or a personal area network.

123. The method of Clause 121, wherein the first controller communicates with the second controller via Bluetooth.

124. The method of Clause 121, wherein the first controller is remote from the second controller and communicates with the second controller via a wide area network.

125. The method of any one of Clauses 121 to 124, wherein the second controller is a smart device.

126. The method of any one of Clauses 79 to 125, wherein:
the at least one controller comprises a first controller, a second controller, and a third controller;
the first controller is integrated with the housing;
the second controller is separate from the housing and communicates with the first controller via a local area network and/or a personal area network;
the third controller is separate from the housing and is one or more remote computing devices.

127. The method of any one of Clauses 79 to 126, further comprising a catheter extending from the housing, the catheter having (a) a proximal end coupled to the housing and in fluid communication with the reservoir, and (b) a distal end configured to be positioned within a blood vessel of a patient.

128. The method of Clause 127, wherein the sensing element is positioned at or near the distal end of the catheter and/or the reservoir.

129. The method of Clause 127, wherein the sensing element is a first sensing element and the method includes a second sensing element positioned at or near the distal end of the catheter and/or the reservoir, wherein the second sensing element is communicatively coupled to the at least one controller.

130. The method of any one of Clauses 79 to 129, wherein the sensing element is integrated with the housing.

131. The method of any one of Clauses 79 to 130, wherein at least a portion of the sensing element is positioned at an exterior surface of the housing.

132. The method of any one of Clauses 79 to 131, wherein:
the sensing element comprises a pulse oximeter configured to emit light;
the housing includes a window and the sensing element is positioned adjacent the window, wherein the window is configured to allow the light emitted from the pulse oximeter to pass through to a location external to the housing.

133. The method of Clause 132, wherein the window is configured to allow reflected light to pass back through.

134. The method of Clause 132 or Clause 133 wherein the window comprises sapphire.

135. The method of any one of Clauses 132 to 134, wherein the window is brazed to the housing.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

The present technology relates to vascular access devices, systems, and methods for monitoring patient health. An overview of the devices, systems, and methods of the present technology are described below with reference to FIGS. 1-3 and Section I. Selected systems and methods of the present technology for monitoring one or more physiological parameters are described below with reference to FIGS. 4-9 and Section II.

I. Overview

Figure 1:
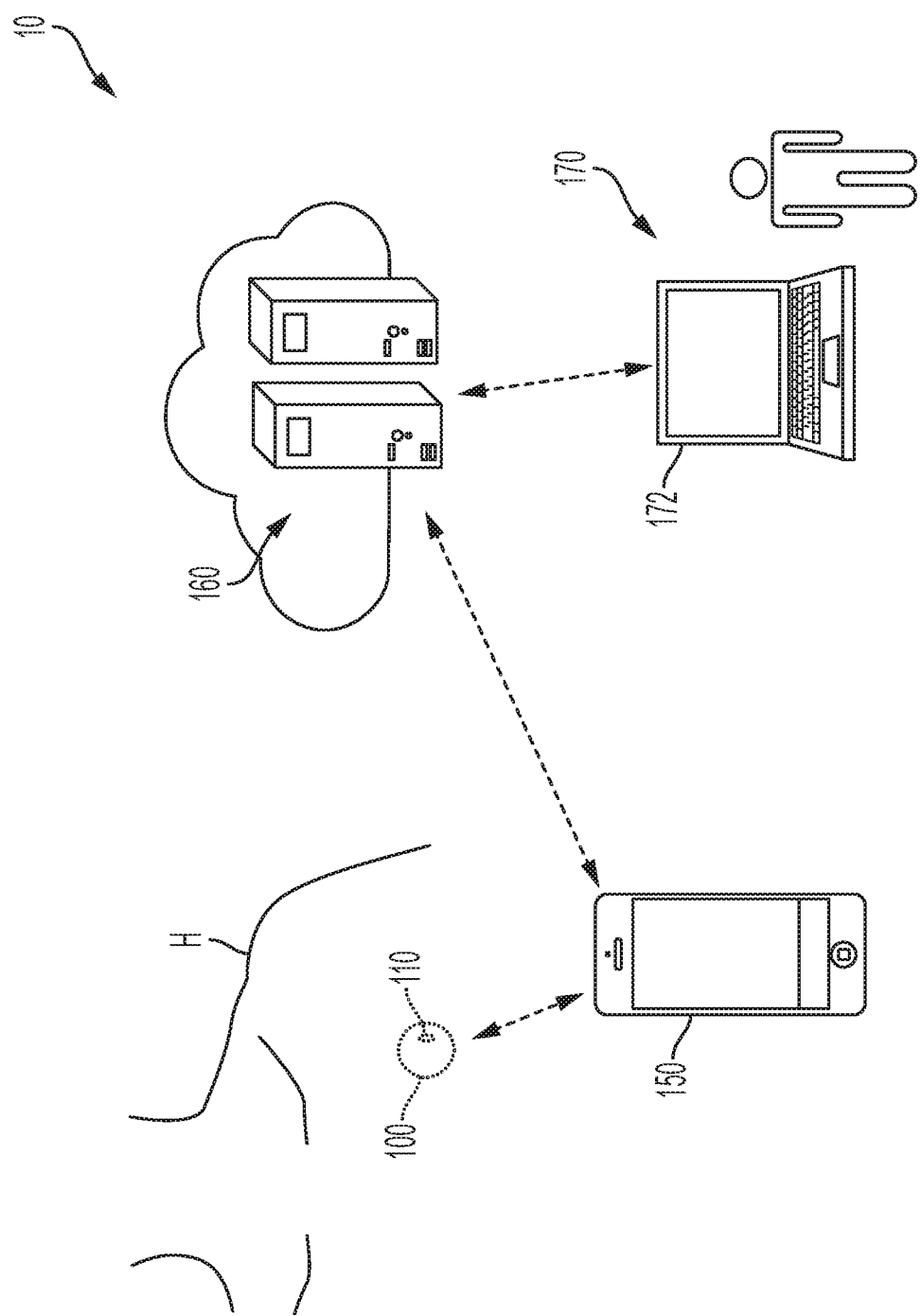
FIG. 1 is a schematic representation of a system for monitoring the health of a patient via an implanted medical device in accordance with the present technology.

FIG. 1 is a schematic representation of a system 10 for monitoring the health of a patient via a vascular access device 100 (or "device 100") in accordance with the present technology. The device 100 is configured to be implanted within a human patient H, such as at a subcutaneous location along an upper region of the patient's chest. As shown in FIG. 1, the device 100 may include a sensing element 110 configured to obtain physiological measurements that are used by the system 10 to determine one or more physiological parameters indicative of the patient's health. In some embodiments, the system 10 may detect a medical condition (such as sepsis) or associated symptom(s) based on the physiological parameter(s) and provide an indication of the detected symptom or condition to the patient, caregiver, and/or medical care team.

As shown schematically in FIG. 1, the device 100 may be configured to communicate wirelessly with a local computing device 150, which can be, for example, a smart device (e.g., a smartphone, a tablet, or other handheld device having a processor and memory), a special-purpose interrogation device, or other suitable device. Communication between the device 100 and the local computing device 150 can be mediated by, for example, near-field communication (NFC), infrared wireless, Bluetooth, ZigBee, Wi-Fi, inductive coupling, capacitive coupling, or any other suitable wireless communication link. The device 100 may transmit data including, for example, physiological measurements obtained via the sensing element 110, patient medical records, device performance metrics (e.g., battery level, error logs, etc.), or any other such data stored by the device 100. In some embodiments, the transmitted data is encrypted or otherwise obfuscated to maintain security during transmission to the local computing device 150. The local computing device 150 may also provide instructions to the vascular access device 100, for example to obtain certain physiological measurements via the sensing element 110, to emit a localization signal, or to perform other functions. In some embodiments, the local computing device 150 may be configured to wirelessly recharge a battery of the device 100, for example via inductive charging.

The system 10 may further include first remote computing device(s) 160 (or server(s)), and the local computing device 150 may in turn be in communication with first remote computing device(s) 160 over a wired or wireless communications link (e.g., the Internet, public and private intranet, a local or extended Wi-Fi network, cell towers, the plain old telephone system (POTS), etc.). The first remote computing device(s) 160 may include one or more own processor(s) and memory. The memory may be a tangible, non-transitory computer-readable medium configured to store instructions executable by the processor(s). The memory may also be configured to function as a remote database, i.e., the memory may be configured to permanently or temporarily store data received from the local computing device 150 (such as one or more physiological measurements or parameters and/or other patient information).

In some embodiments, the first remote computing device(s) 160 can additionally or alternatively include, for example, server computers associated with a hospital, a medical provider, medical records database, insurance company, or other entity charged with securely storing patient data and/or device data. At a remote location 170 (e.g., a hospital, clinic, insurance office, medical records database, operator's home, etc.), an operator may access the data via a second remote computing device 172, which can be, for example a personal computer, smart device (e.g., a smartphone, a tablet, or other handheld device having a processor and memory), or other suitable device. The operator may access the data, for example, via a web-based application. In some embodiments, the obfuscated data provided by the device 100 can be de-obfuscated (e.g., unencrypted) at the remote location 170.

In some embodiments, the device 100 may communicate with remote computing devices 160 and/or 172 without the intermediation of the local computing device 150. For example, the vascular access device 100 may be connected via Wi-Fi or other wireless communications link to a network such as the Internet. In other embodiments, the device 100 may be in communication only with the local computing device 150, which in turn is in communication with remote computing devices 160 and/or 172.

Figure 2:
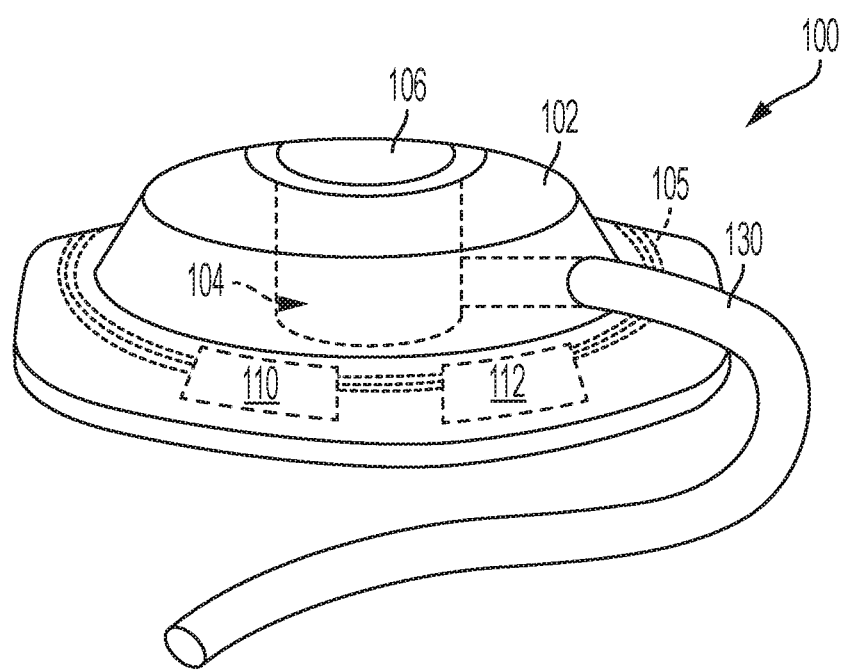
FIG. 2 shows an example of a vascular access device configured for use with the system of FIG. 1.

FIG. 2 shows an example of a vascular access device 100 (or "device 100") configured for use with the system 10 of the present technology. As shown in FIG. 2, the device 100 comprises a housing 102 configured to be implanted within a human patient, a fluid reservoir 104 contained within the housing 102, and a septum 106 adjacent the reservoir 104 and configured to receive a needle therethrough for delivery of a fluid (such as a therapeutic or diagnostic agent) to the reservoir 104 (as described in greater detail below with respect to FIG. 3). The housing 102 may be made of a biocompatible plastic, metal, ceramic, medical grade silicone, or other material that provides sufficient rigidity and strength to prevent needle puncture. The septum 106 can be, for example, a self-sealing membrane made of silicone or other deformable, self-sealing, biocompatible material. In some embodiments, the device 100 may include a catheter 130 that extends distally from the housing 102 and is in fluid communication with the reservoir 104. For example, the catheter 130 can be configured to mate with an outlet port of the device 100 via a barb connector or other suitable mechanical connection. The catheter 130 may be a single or multi-lumen catheter. In some embodiments, the device 100 includes multiple separate catheters.

Figure 3:
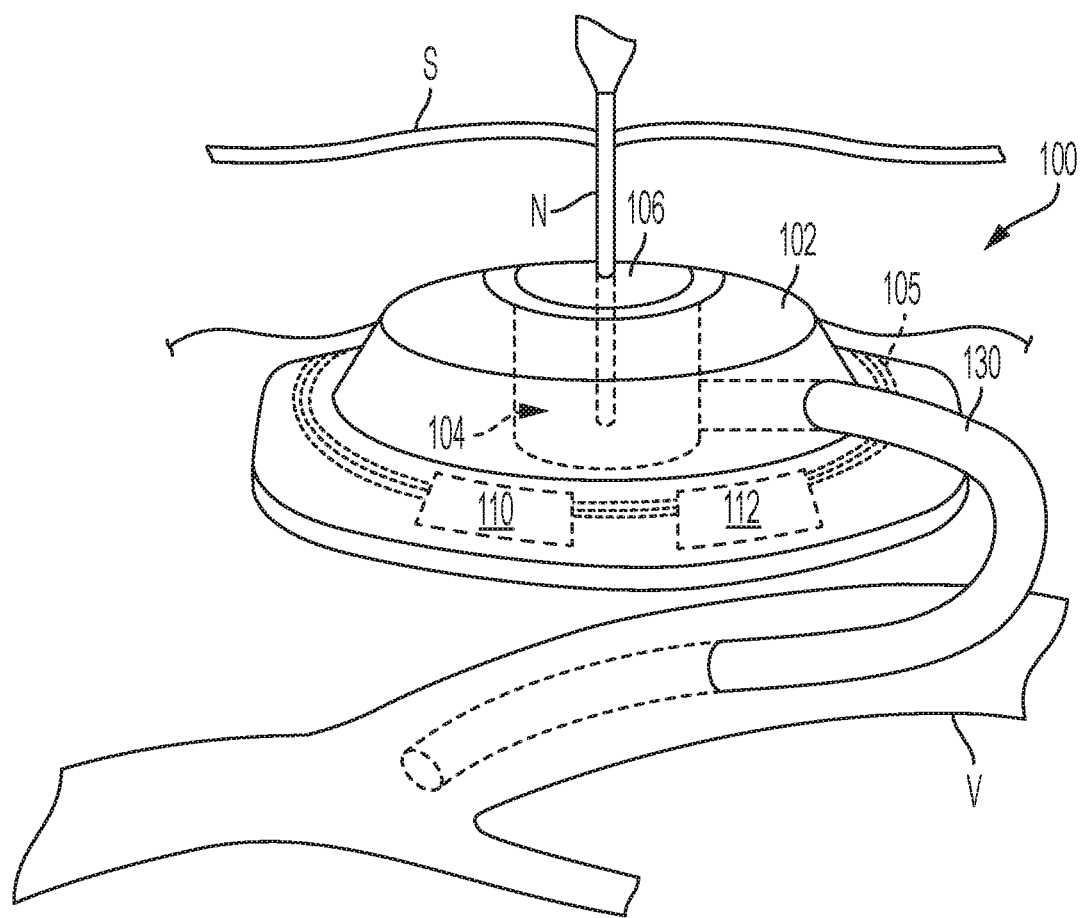
FIG. 3 shows the vascular access device of FIG. 2 implanted within a patient's body.

As shown in FIG. 3, in operation the device 100 is implanted in a patient beneath the skin S, for example in a small pocket created in the upper chest wall just inferior to the clavicle. The catheter 130, which is in fluid communication with the reservoir 104, is inserted into a blood vessel V, for example the internal jugular vein or the subclavian vein with the tip resting in the superior vena cava or the right atrium. A clinician inserts a needle N (e.g., a non-coring or Huber-type needle) through the skin S, through the self-sealing septum 106, and into the fluid reservoir 104. To introduce fluid (e.g., medication) into the patient's blood vessel V, the clinician may advance fluid through the needle N, which then flows through the reservoir 104, the catheter 130, and into the vessel V, or the physician may advance fluid through the needle to fill the reservoir for postponed delivery into the vessel V. To remove fluid from the vessel V (e.g., to aspirate blood from the vessel V for testing), the clinician can apply suction via the needle N, thereby withdrawing fluid (e.g., blood) from the vessel V into the catheter 130, into the fluid reservoir 104, and into the needle N. When the procedure is completed, the clinician removes the needle N, the self-sealing septum 106 resumes a closed configuration, and the device 100 may remain in place beneath the patient's skin S.

Referring again to FIG. 2, as previously mentioned, the device 10 includes a sensing element 110 coupled to the housing 102 and configured to obtain physiological measurements. Although a single sensing element 110 is illustrated for clarity, in various embodiments, the device 100 may include a plurality of sensing elements 110 disposed within or otherwise coupled to the housing 102. In some embodiments, one or more such sensing elements 110 may be disposed on separate structural components that are separated from the housing 102. As used herein, the term "sensing element" may refer to a single sensor or a plurality of discrete, separate sensors.

The device 100 may include at least one controller 112 communicatively coupled to the sensing element 110. The controller 112 may include one or more processors, software components, and memory (not shown). In some examples, the one or more processors include one or more computing components configured to process the physiological measurements received from the sensing element 110 according to instructions stored in the memory. The memory may be a tangible, non-transitory computer-readable medium configured to store instructions executable by the one or more processors. For instance, the memory may be data storage that can be loaded with one or more of the software components executable by the one or more processors to achieve certain functions. In some examples, the functions may involve causing the sensing element 110 to obtain physiological data from the patient. In another example, the functions may involve processing the physiological data to determine one or more physiological parameters and/or provide an indication to the patient and/or clinician of one or more symptoms or medical conditions associated with the determined physiological parameters or symptoms.

The controller 112 may also include a data communications unit configured to securely transmit data between the device 100 and external computing devices (e.g., local computing device 150, remote computing devices 160 and 170, etc.). In some embodiments, the controller 112 includes a localization unit configured to emit a localization signal (e.g., lights that transilluminate a patient's skin, vibration, a magnetic field, etc.) to aid a clinician in localizing the device 100 when implanted within a patient. The controller 112 can also include a wireless charging unit (such as a coil) configured to recharge a battery (not shown) of the device 100 when in the presence of an interrogation device (e.g., local device 150 or another suitable device).

The system 10 may be configured to continuously and/or periodically obtain physiological measurements via the sensing element 110 in communication with the device 100. The sensing element 110 may be carried by the housing 102 and/or the catheter 130, and/or may include a sensing component separate from the housing 102 and catheter 130 but physically or communicatively coupled to the housing 102 and/or catheter 130. The sensing element 110 may be implanted at the same location as the device 100 or at a different location, or may be positioned on the patient at an exterior location (e.g., on the patient's skin). The sensing element 110 may be permanently coupled to the device 100, or may be configured to temporarily couple to the device 100.

In some embodiments, the sensing element 110 is built into the housing 102 such that only a portion of the sensing element 110 is exposed to the local physiological environment when the device 100 is implanted. For example, the sensing element 110 may comprise one or more electrodes having an external portion positioned at an exterior surface of the housing 102 and an internal portion positioned within the housing 102 and wired to the controller 112. In some embodiments, the sensing element 110 may comprise one or more electrodes having an internal portion positioned at an interior surface of the housing 102 at the interface with the port reservoir 104 or junction of the reservoir 104 and the catheter 130, or extending into the catheter 130.

In some embodiments the sensing element 110 may be completely contained within the housing 102. For example, the sensing element 110 may comprise a pulse oximeter enclosed by the housing 102 and positioned adjacent a window in the housing 102 through which light emitted from the pulse oximeter may pass to an external location, and back through which light reflected from the external location may pass for detection by a photodiode of the pulse oximeter. In such embodiments the window may be, for example, a sapphire window that is brazed into place within an exterior wall of the housing 102.

The sensing element 110 may comprise at least one sensor completely enclosed by the housing 102 and at least one sensor that is partially or completely positioned at an external location, whether directly on the housing 102 and/or catheter 130 or separated from the housing 102 and/or catheter 130 (but still physically coupled to the housing 102 and/or catheter 130 via a wired connection, for example.) In some embodiments, at least a portion of the sensing element 110 is positioned at and/or exposed to an interior region of the reservoir 104.

In some embodiments, the sensing element 110 may include a separate controller (not shown) that comprises one or more processors and/or software components. In such embodiments, the sensing element 110 may process at least some of the physiological measurements to determine one or more physiological parameters, and then transmit those physiological parameters to the controller 112 of the device 100 (with or without the underlying physiological data). In some examples, the sensing element 110 may only partially process at least some of the physiological measurements before transmitting the data to the controller 112. In such embodiments, the controller 112 may further process the received physiological data to determine one or more physiological parameters. The local computing device 150 and/or the remote computing devices 160, 170 may also process some or all of the physiological measurements obtained by the sensing element 110 and/or physiological parameters determined by the sensing element 110 and/or the controller 112.

According to some aspects of the technology, the sensing element 110 may include memory. The memory may be a non-transitory computer-readable medium configured to permanently and/or temporarily store the physiological measurements obtained by the sensing element 110. In those embodiments where the sensing element 110 includes its own processor(s), the memory may be a tangible, non-transitory computer-readable medium configured to store instructions executable by the processor(s).

In some embodiments, the sensing element(s) 110 and/or controller 112 may identify, monitor, and communicate patient information by electromagnetic, acoustic, motion, optical, thermal, or biochemical sensing elements or means. The sensing element(s) 110 may include, for example, one or more temperature sensing elements (e.g., one or more thermocouples, one or more digital temperature sensors, one or more thermistors or other type of resistance temperature detector, etc.), one or more impedance sensing elements (e.g., one or more electrodes), one or more pressure sensing elements, one or more optical sensing elements, one or more flow sensing elements (e.g., a Doppler velocity sensing element, an ultrasonic flow meter, etc.), one or more ultrasonic sensing elements, one or more pulse oximeters, one or more chemical sensing elements, one or more movement sensing elements (e.g., one or more accelerometers), one or more pH sensing elements, an electrocardiogram ("ECG" or "EKG") unit, one or more electrochemical sensing elements, one or more hemodynamic sensing elements, and/or other suitable sensing devices.

The sensing element 110 may comprise one or more electromagnetic sensing elements configured to measure and/or detect, for example, impedance, voltage, current, or magnetic field sensing capability with a wire, wires, wire bundle, magnetic node, and/or array of nodes. The sensing element 110 may comprise one or more acoustic sensing elements configured to measure and/or detect, for example, sound frequency, within human auditory range or below or above frequencies of human auditory range, beat or pulse pattern, tonal pitch melody, and/or song. The sensing element 110 may comprise one or more motion sensing elements configured to measure and/or detect, for example, vibration, movement pulse, pattern or rhythm of movement, intensity of movement, and/or speed of movement. Motion communication may occur by a recognizable response to a signal. This response may be by vibration, pulse, movement pattern, direction, acceleration, or rate of movement. Motion communication may also be by lack of response, in which case a physical signal, vibration, or bump to the environment yields a motion response in the surrounding tissue that can be distinguished from the motion response of the sensing element 110. Motion communication may also be by characteristic input signal and responding resonance. The sensing element 110 may comprise one or more optical sensing elements which may include, for example, illuminating light wavelength, light intensity, on/off light pulse frequency, on/off light pulse pattern, passive glow or active glow when illuminated with special light such as UV or "black light", or display of recognizable shapes or characters. It also includes characterization by spectroscopy, interferometry, response to infrared illumination, and/or optical coherence tomography. The sensing element 110 may comprise one or more thermal sensing elements configured to measure and/or detect, for example, device 100 temperature relative to surrounding environment, the temperature of the device 100 (or portion thereof), the temperature of the environment surrounding the device 100 and/or sensing element 110, or differential rate of the device temperature change relative to surroundings when the device environment is heated or cooled by external means. The sensing element 110 may comprise one or more biochemical devices which may include, for example, the use of a catheter, a tubule, wicking paper, or wicking fiber to enable micro-fluidic transport of bodily fluid for sensing of protein, RNA, DNA, antigen, and/or virus with a micro-array chip.

In some aspects of the technology, the controller 112 and/or sensing element 110 may be configured to detect and/or measure the concentration of blood constituents, such as sodium, potassium, chloride, bicarbonate, creatinine, blood urea nitrogen, calcium, magnesium, and phosphorus. The system 10 and/or the sensing element 110 may be configured to evaluate liver function (e.g., by evaluation and/or detection of AST, ALT, alkaline phosphatase, gamma glutamyl transferase, troponin, etc.), heart function (e.g., by evaluation and/or detection of troponin), coagulation (e.g., via determination of prothrombin time (PT), partial thromboplastin time (PTT), and international normalized ratio (INR)), and/or blood counts (e.g., hemoglobin or hematocrit, white blood cell levels with differential, and platelets). In some embodiments, the system 10 and/or the sensing element 110 may be configured to detect and/or measure circulating tumor cells, circulating tumor DNA, circulating RNA, multigene sequencing of germ line or tumor DNA, markers of inflammation such as cytokines, C reactive protein, erythrocyte sedimentation rate, tumor markers (PSA, beta-HCG, AFP, LDH, CA 125, CA 19-9, CEA, etc.), and others.

As previously mentioned, the system 10 may determine one or more physiological parameters based on the physiological measurements and/or one or more other physiological parameter(s). For example, the system 10 may be configured to determine physiological parameters such as heart rate, temperature, blood pressure (e.g., systolic blood pressure, diastolic blood pressure, mean blood pressure), blood flow rate, blood velocity, pulse wave speed, volumetric flow rate, reflected pressure wave amplitude, augmentation index, flow reserve, resistance reserve, resistive index, capacitance reserve, hematocrit, heart rhythm, electrocardiogram (ECG) tracings, body fat percentage, activity level, body movement, falls, gait analysis, seizure activity, blood glucose levels, drug/medication levels, blood gas constituents and blood gas levels (e.g., oxygen, carbon dioxide, etc.), lactate levels, hormone levels (such as cortisol, thyroid hormone (T4, T3, free T4, free T3), TSH, ACTH, parathyroid hormone), and/or any correlates and/or derivatives of the foregoing measurements and parameters (e.g., raw data values, including voltages and/or other directly measured values). In some embodiments, one or more of the physiological measurements can be utilized or characterized as a physiological parameter without any additional processing by the system 10.

The system 10 may also determine and/or monitor derivatives of any of the foregoing physiological parameters (also referred to herein as "physiological parameters"), such as a rate of change of a particular parameter, a change in a particular parameter over a particular time frame, etc. As but a few examples, the system 10 may be configured to determine as temperature over a specified time, a maximum temperature, a maximum average temperature, a minimum temperature, a temperature at a predetermined or calculated time relative to a predetermined or calculated temperature, an average temperature over a specified time, a maximum blood flow, a minimum blood flow, a blood flow at a predetermined or calculated time relative to a predetermined or calculated blood flow, an average blood flow over time, a maximum impedance, a minimum impedance, an impedance at a predetermined or calculated time relative to a predetermined or calculated impedance, a change in impedance over a specified time, a change in impedance relative to a change in temperature over a specified time, a change in heart rate over time, a change in respiratory rate over time, activity level over a specified time and/or at a specified time of day, and other suitable derivatives.

Measurements may be obtained continuously or periodically at one or more predetermined times, ranges of times, calculated times, and/or times when or relative to when a measured event occurs. Likewise, physiological parameters may be determined continuously or periodically at one or more predetermined times, ranges of times, calculated times, and/or times when or relative to when a measured event occurs.

Based on the determined physiological parameters, the system 10 of the present technology is configured to provide an indication of the patient's health to the patient and/or a clinician. For example, the controller 112 may compare one or more of the physiological parameters to a predetermined threshold or range and, based on the comparison, provide an indication of the patient's health. For instance, if the determined physiological parameter(s) is above or below the predetermined threshold or outside of the predetermined range, the system 10 may provide an indication that the patient is at risk of, or has already developed, a medical condition characterized by symptoms associated with the determined physiological parameters. As used herein, a "predetermined range" refers to a set range of values, and "outside of a/the predetermined range" refers to (a) a measured or calculated range of values that only partially overlap the predetermined range or do not overlap any portion of a predetermined range of values. As used herein, a "predetermined threshold" refers to a single value or range of values, and a parameter that is "outside" of "a predetermined threshold" refers to a situation where the parameter is (a) a measured or calculated value that exceeds or fails to meet a predetermined value, (b) a measured or calculated value that falls outside of a predetermined range of values, (c) a measured or calculated range of values that only partially overlaps a predetermined range of values or does not overlap any portion of a predetermined range of values, or (d) a measured or calculated range of values where none of the values overlap with a predetermined value.

Predetermined parameter thresholds and/or ranges can be empirically determined to create a look-up table. Look-up table values can be empirically determined, for example, based on clinical studies and/or known healthy or normal values or ranges of values. The predetermined threshold may additionally or alternatively be based on a particular patient's baseline physiological parameters.

Medical conditions detected and/or indicated by the system 10 may include, for example, sepsis, pulmonary embolism, metastatic spinal cord compression, anemia, dehydration/volume depletion, vomiting, pneumonia, congestive heart failure, performance status, arrythmia, neutropenic fever, acute myocardial infarction, pain, opioid toxicity, nicotine or other drug addiction or dependency, hyperglycemic/diabetic ketoacidosis, hypoglycemia, hyperkalemia, hypercalcemia, hyponatremia, one or more brain metastases, superior vena cava syndrome, gastrointestinal hemorrhage, immunotherapy-induced or radiation pneumonitis, immunotherapy-induced colitis, diarrhea, cerebrovascular accident, stroke, pathological fracture, hemoptysis, hematemesis, medication-induced QT prolongation, heart block, tumor lysis syndrome, sickle cell anemia crisis, gastroparesis/cyclic vomiting syndrome, hemophilia, cystic fibrosis, chronic pain, and/or seizure.

For the purposes of this specification and appended claims, unless otherwise indicated, all numbers expressing temperatures, percentage changes in physiological parameters, concentration of blood constituents, heart rate, respiratory rate, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a sensing element" includes one, two, three or more sensing elements.

As used herein, the term "at least one of A, B, and C" means any of A, B, or C individually, as well as any combination of two or more of A, B, and C. For example, "at least one of A, B, and C" includes A, B, C, AB, AC, BC, and ABC.

II. Selected Devices, Systems, and Methods for Monitoring Patient Health

Figure 4:
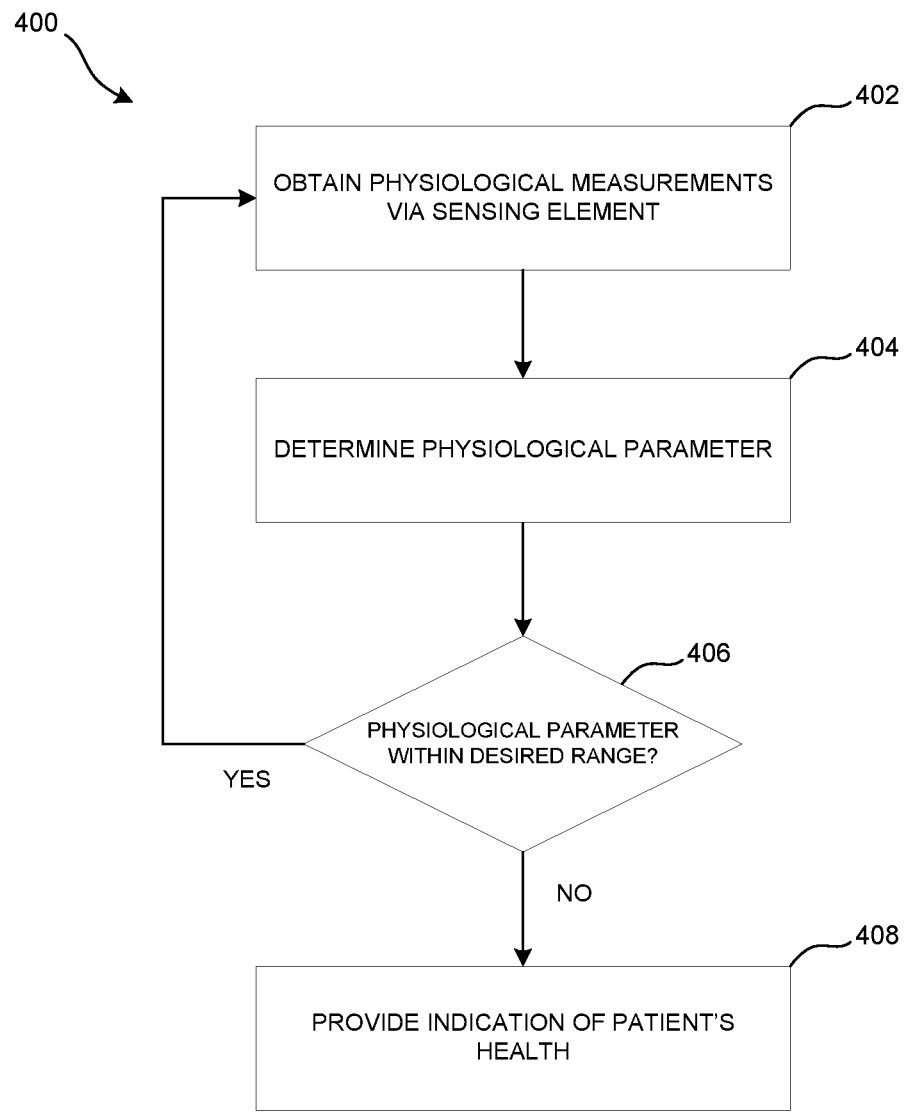
FIG. 4 is a flow diagram of a process configured to determine one or more physiological parameters in accordance with the present technology.

FIG. 4 shows a process 400 configured to determine one or more physiological parameters and provide an indication of one or more medical conditions, which includes an indication that the patient is developing or at risk of developing a medical condition, as well as an indication that the patient has already developed the medical condition. The process 400 can be implemented by one or more aspects of the system of the present technology (such as system 10). In some embodiments, the process 400 comprises one or more instructions stored in memory (e.g., the memory of the device 100 and/or the memory of the sensing element 110) and executed by one or more processors (e.g., the controller 112, the controller of the sensing element 110, a processor of the local computing device 150 (FIG. 1), a processor of the remote computing device(s) 160, and/or a processor of the remote computing device(s) 170) of a monitoring system (e.g., system 10).

Various embodiments of the process 400 include one or more operations, functions, and actions illustrated by blocks 402 through 408. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

In addition, for the process 400 and other processes and methods disclosed herein, the flowchart shows functionality and operation of one possible implementation of some embodiments. In this regard, each block may represent a module, a segment, or a portion of program code, which includes one or more instructions executable by one or more processors for implementing specific logical functions or steps in the process. The program code may be stored on any type of computer readable medium, for example, such as a storage device including a disk or hard drive. The computer readable medium may include non-transitory computer readable media, for example, such as tangible, non-transitory computer-readable media that stores data for short periods of time like register memory, processor cache, and Random-Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the process 400 and other processes and methods disclosed herein, each block in FIG. 4 may represent circuitry that is wired to perform the specific logical functions in the process.

At block 402, the process 400 obtains physiological measurements via a sensing element (such as any of the sensing elements 110 described herein) coupled to a vascular access device (such as any of the vascular access devices 100 described herein) while the device is implanted within the patient. At block 404, the process 400 may determine at least one physiological parameter (such as any of the physiological parameters described herein) based on the physiological measurements. At block 406, the process 400 may compare the at least one physiological parameter to a predetermined threshold and, based on the comparison, cause the system 10 to provide an indication of the patient's health (block 408). For example, if the determined physiological parameter(s) is outside of a predetermined threshold, the system 10 may provide an indication that the patient is at risk of, or has already developed, a medical condition characterized by symptoms associated with the determined physiological parameters. The indication may be an auditory indication (e.g., a bell or chime, a verbal communication, etc.) and/or a visual indication (e.g., text, emitting light, etc.) communicated locally via the local computing device 150 (FIG. 1) and/or remotely via the remote computing device 170 (FIG. 1). In some embodiments, the process 400 may determine the particular medical condition or potential medical conditions indicated by the physiological parameters and communicate those condition(s) via the indication. In some embodiments, the process 400 may not explicitly communicate the particular condition in the indication but still provide an alert that the patient's data needs review by a medical professional.

In some embodiments, the process 400 may cause an indication of the patient's health even when the physiological parameters are within a predetermined threshold. For example, the process 400 may provide regular health updates via the local computing device 150 (FIG. 1) and/or remote computing device 170 (FIG. 1), which may include a simple report of certain ones of the patient's physiological parameters and/or an assessment of one or more of the parameters.

A. Sepsis

The most common group of patients to have an implanted vascular access port are cancer patients undergoing chemotherapy. Chemotherapy comes with a long list of side effects, one of which is a weakened immune system and a corresponding increased risk of contracting an infection. Cancer patients are particularly susceptible to sepsis, which is a life-threatening condition where the body's response to infection injures the patient's tissues and organs. The system of the present technology is configured to determine one or more physiological parameters indicative of sepsis and provide an indication to the patient and/or physician that indicates that the patient is septic or progressing toward sepsis (such as an indication of systemic inflammatory response syndrome ("SIRS")). As used herein in the specification and the claims, an indication that the patient is septic includes an indication that the patient is progressing towards sepsis.

Figure 5:
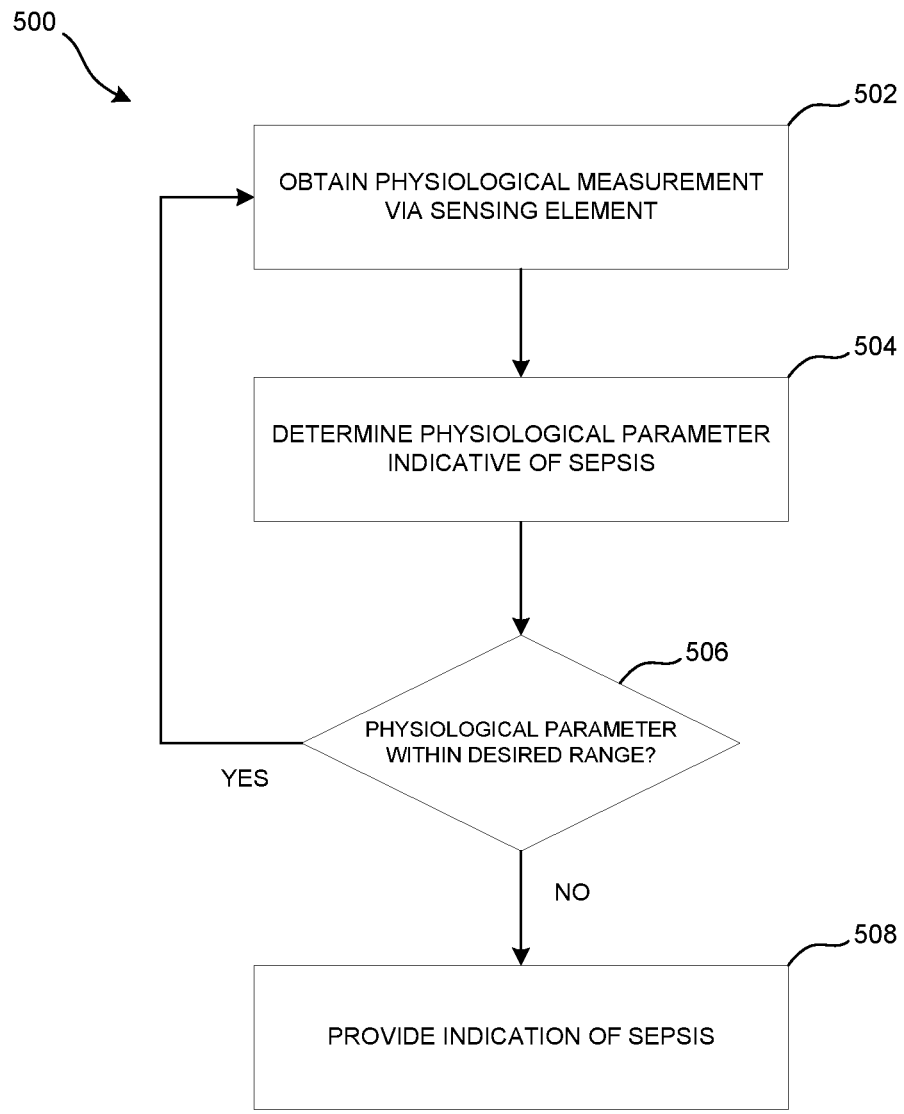
FIG. 5 is a flow diagram of a process configured to determine one or more physiological parameters and provide an indication of sepsis in accordance with the present technology.

FIG. 5, for example, shows a process 500 configured to determine one or more physiological parameters characterizing sepsis (and/or one or more corresponding symptoms) and provide an indication of sepsis to the patient and/or physician. The process 500 can be implemented by one or more aspects of the system of the present technology (such as system 10). In some embodiments, the process 500 comprises one or more instructions stored in memory (e.g., the memory of the device 100 and/or the memory of the sensing element 110) and executed by one or more processors (e.g., the controller 112, the controller of the sensing element 110, a processor of the local computing device 150 (FIG. 1), a processor of the remote computing device(s) 160, and/or a processor of the remote computing device(s) 170) of a monitoring system (e.g., system 10).

Various embodiments of the process 500 include one or more operations, functions, and actions illustrated by blocks 502 through 508. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

In addition, for the process 500 and other processes and methods disclosed herein, the flowchart shows functionality and operation of one possible implementation of some embodiments. In this regard, each block may represent a module, a segment, or a portion of program code, which includes one or more instructions executable by one or more processors for implementing specific logical functions or steps in the process. The program code may be stored on any type of computer readable medium, for example, such as a storage device including a disk or hard drive. The computer readable medium may include non-transitory computer readable media, for example, such as tangible, non-transitory computer-readable media that stores data for short periods of time like register memory, processor cache, and Random-Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the process 400 and other processes and methods disclosed herein, each block in FIG. 5 may represent circuitry that is wired to perform the specific logical functions in the process.

At block 502, the process 500 obtains physiological measurements via a sensing element (such as any of the sensing elements 110 described herein) coupled to a vascular access device (such as any of the vascular access devices 100 described herein) while the device is implanted within the patient. The physiological measurements may include at least temperature, for example. Based on the physiological measurements, the process 500 may determine at least one physiological parameter indicative of sepsis (block 504), such as at least one of a temperature parameter, a heart rate parameter, a respiratory rate parameter, and an activity level parameter, each of which is discussed in greater detail below.

A common symptom of sepsis is a measured body temperature outside of a normal range (i.e., hypothermia or a fever). Accordingly, the system of the present technology is configured to determine a temperature parameter, such as instantaneous body temperature, a change in body temperature over time, a rate of change in body temperature over time, an average body temperature over time, etc. As shown in FIG. 5, if the process 500 determines at block 506 that the temperature parameter is outside of the predetermined temperature threshold, then the process 500 may provide an indication that the patient is septic. For example, the process

500 may provide an indication that the patient is septic if the process 500 determines (a) a body temperature of the patient is outside of a predetermined temperature threshold of 96-100° F., 95-100° F.; or 95-101.3° F.; (b) a body temperature is outside of a predetermined threshold of 96-100° F., 95-100° F.; or 95-101.3° F. for a predetermined amount of time; (c) an instantaneous or average body temperature is greater than 100° F. or 101° F.; (d) an instantaneous or average body temperature is greater than 100° F. or 101° F. for a predetermined amount of time; (e) an instantaneous or average body temperature is less than 96° F. or 95° F.; (f) an instantaneous or average body temperature is less than 96° F. or 95° F. for a predetermined amount of time; (g) at least a 2% change in body temperature from a baseline temperature; and/or (h) at least a 2% change in body temperature from a baseline temperature over a predetermined amount of time.

Another common symptom of sepsis is tachycardia, or increased heart rate. Accordingly, the system of the present technology is configured to determine a heart rate parameter, such as a heart rate of the patient. As shown in FIG. 5, if the process 500 determines at block 506 that each of the temperature parameter and the heart rate parameter are outside of corresponding predetermined thresholds, then the process 500 may provide an indication that the patient is septic. For example, the process 500 may provide an indication that the patient is septic if the process 500 determines the temperature parameter is outside of a predetermined temperature threshold, and if (a) the heart rate of the patient is greater than 90 beats per minute, 95 beats per minute, or 100 beats per minute; (b) the heart rate of the patient is greater than 90 beats per minute, 95 beats per minute, or 100 beats per minute for a predetermined amount of time; (c) the heart rate of the patient increases at least 10%, 15%, 20%, or 25% from a reference heart rate of the patient; and/or (d) the heart rate of the patient increases at least 10%, 15%, 20%, or 25% from a reference heart rate of the patient over a predetermined amount of time.

Another common symptom of sepsis is increased respiratory rate. Accordingly, the system of the present technology is configured to determine a respiratory rate parameter, such as a respiratory rate of the patient. As shown in FIG. 5, if the process 500 determines at block 506 that each of the temperature parameter and the respiratory rate parameter are outside of corresponding predetermined thresholds, then the process 500 may provide an indication that the patient is septic. For example, the process 500 may provide an indication that the patient is septic if the process 500 determines the temperature parameter is outside of a predetermined temperature threshold, and if (a) the respiratory rate of the patient is greater than 15, 16, 17, 18, 19, 20, 21, or 22 breaths per minute, and/or (b) the respiratory rate of the patient is greater than 15, 16, 17, 18, 19, 20, 21, or 22 breaths per minute for a predetermined amount of time.

Another common symptom of sepsis is decreased activity level. Accordingly, the system of the present technology is configured to determine a movement parameter. The sensing element 110, for example, may include an accelerometer or other sensor configured to detect and/or measure movement (or derivatives thereof), and the physiological measurements may include at least movement of the patient. The process 700 may also include measurements obtained by one or more movement detection elements positioned or worn at locations on the patient's body separate from the device 100.

Based on the physiological measurements, the process 500 may determine at least one movement parameter and/or a performance status, such as any of the movement parameters and performance statuses described below with respect to FIG. 7.

As shown in FIG. 5, if the process 500 determines at block 506 that each of the temperature parameter and the movement parameter are outside of corresponding predetermined thresholds, then the process 500 may provide an indication that the patient is septic. For example, the process 500 may provide an indication that the patient is septic if the process 500 determines the temperature parameter is outside of a predetermined temperature threshold (above or below), and a movement parameter of the patient is less than a predetermined threshold, as septic patients are lethargic and less active. The predetermined threshold, for example, may be based on a baseline activity level of the patient.

The process 500 may also determine one or more additional physiological parameters indicative of sepsis, such as central venous pressure. The process 500 may provide an indication that the patient is septic, for example, by determining the central venous pressure is below 2 mm/Hg.

In some embodiments, the system 10 may be configured to obtain and store a blood sample from the patient for later analysis. For example, the device 10 may include one or more discrete receptacles for temporarily storing blood. The receptacles may be contained within the housing, or may be separate compartments fluidly coupled to the catheter 130 and/or the housing 102. In some embodiments, the device 10 may contain a first catheter coupled to the reservoir (such as catheter 130) and a second catheter coupled to the receptacle(s). The device 10 may be configured to draw blood at pre-set times or at pre-set intervals, or in response to detection of one or more systems or medical conditions. As it relates to sepsis, the blood sample(s) obtained by the system may be saved for later analysis to determine one or more indicators of sepsis, such as a blood pH less than 7.2, a serum lactate greater than 2 mmol/L, 3 mmol/L, or 4 mmol/L, and/or a procalcitonin level above 2 ng/mL.

B. Congestive Heart Failure

Congestive heart failure ("CHF") is a progressive, life-threatening condition in which the heart muscles are weakened and cannot pump blood sufficiently to maintain blood flow to meet the body's needs. Additionally, there are several causes of acute congestive heart failure such as acute myocardial infarction and heart block. Cancer patients are specifically at risk of hypercoagulability and thus formation of deep venous thrombosis and pulmonary embolism. Therefore, in the oncology patient, pulmonary embolism represents a common cause of acute CHF and as such detection of acute CHF can be a surrogate clinical marker for acute pulmonary embolism. The system of the present technology is configured to determine one or more physiological parameters indicative of CHF and provide an indication to the patient and/or physician that indicates that the patient has CHF.

Figure 6:
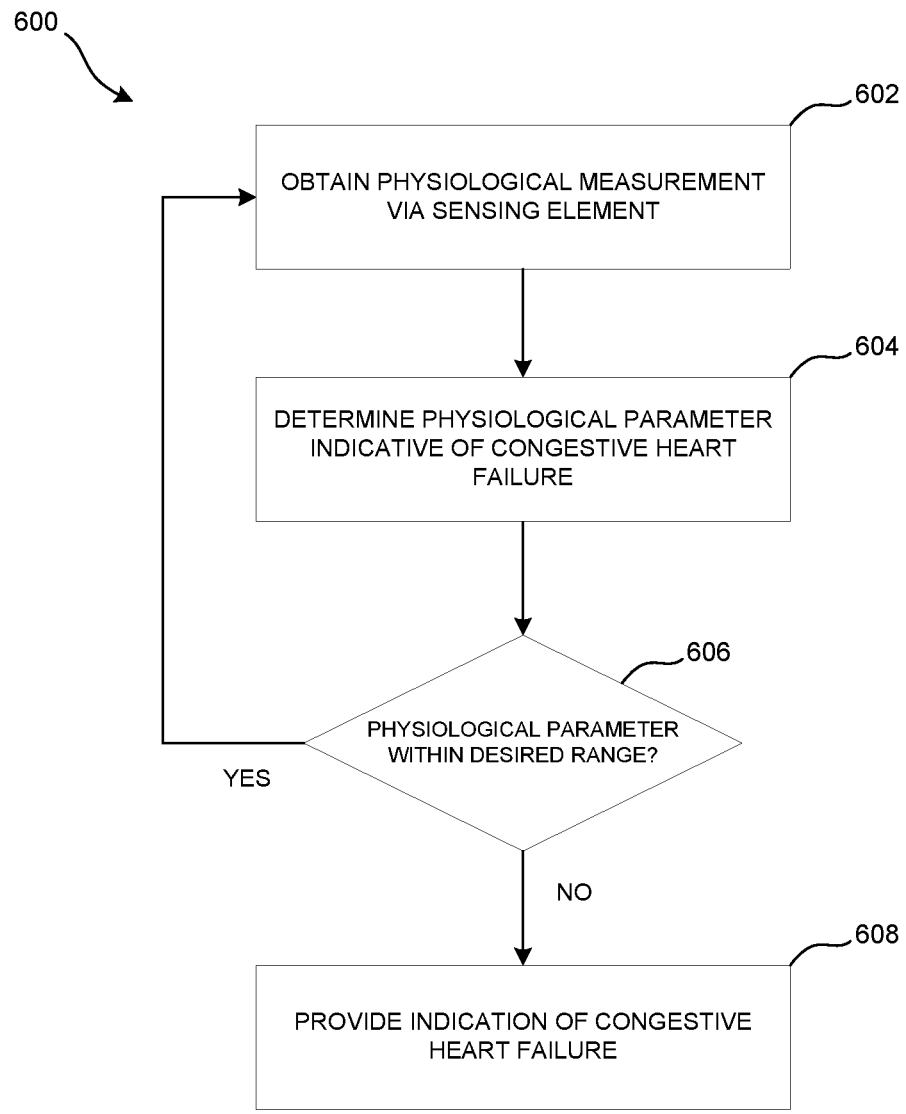
FIG. 6 is a flow diagram of a process configured to determine one or more physiological parameters and provide an indication of congestive heart failure in accordance with the present technology.

FIG. 6, for example, shows a process 600 configured to determine one or more physiological parameters characterizing CHF (and/or one or more corresponding symptoms) and provide an indication of CHF to the patient and/or physician. The process 600 can be implemented by one or more aspects of the system of the present technology (such as system 10). In some embodiments, the process 600 comprises one or more instructions stored in memory (e.g., the memory of the device 100 and/or the memory of the sensing element 110) and executed by one or more processors (e.g., the controller 112, the controller of the sensing element 110, a processor of the local computing device 150 (FIG. 1), a processor of the remote computing device(s) 160, and/or a processor of the remote computing device(s) 170 of a monitoring system (e.g., system 10).

Various embodiments of the process 600 include one or more operations, functions, and actions illustrated by blocks 602 through 608. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

In addition, for the process 600 and other processes and methods disclosed herein, the flowchart shows functionality and operation of one possible implementation of some embodiments. In this regard, each block may represent a module, a segment, or a portion of program code, which includes one or more instructions executable by one or more processors for implementing specific logical functions or steps in the process. The program code may be stored on any type of computer readable medium, for example, such as a storage device including a disk or hard drive. The computer readable medium may include non-transitory computer readable media, for example, such as tangible, non-transitory computer-readable media that stores data for short periods of time like register memory, processor cache, and Random-Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the process 600 and other processes and methods disclosed herein, each block in FIG. 6 may represent circuitry that is wired to perform the specific logical functions in the process.

At block 602, the process 600 obtains physiological measurements via a sensing element (such as any of the sensing elements 110 described herein) coupled to a vascular access device (such as any of the vascular access devices 100 described herein) while the device is implanted within the patient. The physiological measurements may include at least pressure and/or electrical activity, for example. Based on the physiological measurements, the process 600 may determine at least one physiological parameter indicative of CHF (block 604), such as at least one of a central venous pressure ("CVP"), an oxygen saturation parameter, a heart rate parameter, a heart rhythm parameter, a respiratory rate parameter, and an activity level parameter, each of which is discussed in greater detail below.

A common symptom of CHF is increased central venous pressure ("CVP"). CVP is considered a direct measurement of the blood pressure in the right atrium and vena cava, and essentially reflects the amount of blood returning to the heart and the ability of the heart to pump the blood back into the arterial system. To measure CVP, the sensing element 110 may include a pressure sensing element (such as a pressure transducer) located at a distal portion of the catheter 130 and/or in the reservoir 104. In some embodiments, the system 10 may include an additional catheter with a distal portion configured to be positioned in the lower third of the superior vena cava or the right atrium, and the pressure transducer may be positioned at the distal portion of the additional catheter.

The process 600 may be configured to determine CVP based on the physiological measurements obtained by the sensing element 110. As shown in FIG. 6, if the process 600 determines at block 606 that the patient's CVP is outside of the predetermined temperature threshold, then the process 600 may provide an indication that the patient has CHF. For example, the process 600 may provide an indication that the patient has CHF if the process 600 determines the CVP is greater than 4 mm Hg, 5 mm Hg, or 6 mm Hg.

In addition to CVP, the process 600 may also determine one or more additional physiological parameters indicative of CHF, such as: (a) oxygen saturation less than a baseline or other predetermined threshold, (b) heart rate greater than baseline or other predetermined threshold (as the patient's heart rate increases in an attempt to maintain cardiac output); (c) irregular heart rhythm; (d) a respiratory rate greater than baseline or other predetermined threshold (e.g., greater than 15, 16, 17, 18, 19, 20, 21, or 22 breaths per minute); and/or (d) high or low blood pressure. As used herein, "low blood pressure" refers to a blood pressure lower than 90 mm Hg systolic or 60 mm Hg diastolic. As used here, "high blood pressure" refers to a blood pressure between 120-129 mm Hg systolic and less than 80 mm Hg diastolic, or between 130-139 mm Hg systolic or between 80-89 mm Hg diastolic, or at least 140 mm Hg systolic or at least 90 mm Hg diastolic, or over 180 mm Hg systolic and/or over 120 mm Hg diastolic.

C. Performance Status

Hospitals, cancer centers, and clinics require the use of standard criteria for measuring how a disease impacts a patient's daily living abilities (known to physicians and researchers as a patient's performance status). Performance status is highly correlated with survival outcomes. One method of evaluating performance status is the Eastern Cooperative Oncology Group ("ECOG") Scale, which describes a patient's level of functioning in terms of their ability to care for them self, daily activity, and physical ability (walking, working, etc.). The ECOG Scale includes the following categories: (0) Fully active, able to carry on all pre-disease performance without restriction; (1) restricted in physically strenuous activity but ambulatory and able to carry out work of a light or sedentary nature, e.g., light house work, office work; (2) ambulatory and capable of all selfcare but unable to carry out any work activities; up and about more than 50% of waking hours; (3) capable of only limited selfcare; confined to bed or chair more than 50% of waking hours; (4) completely disabled; cannot carry on any selfcare; totally confined to bed or chair; (5) dead. The devices, systems, and methods of the present technology may also be used to assess and provide indications of performance status based on methods other than the ECOG Scale, such as the Karnofsky Performance Status and others.

Figure 7:
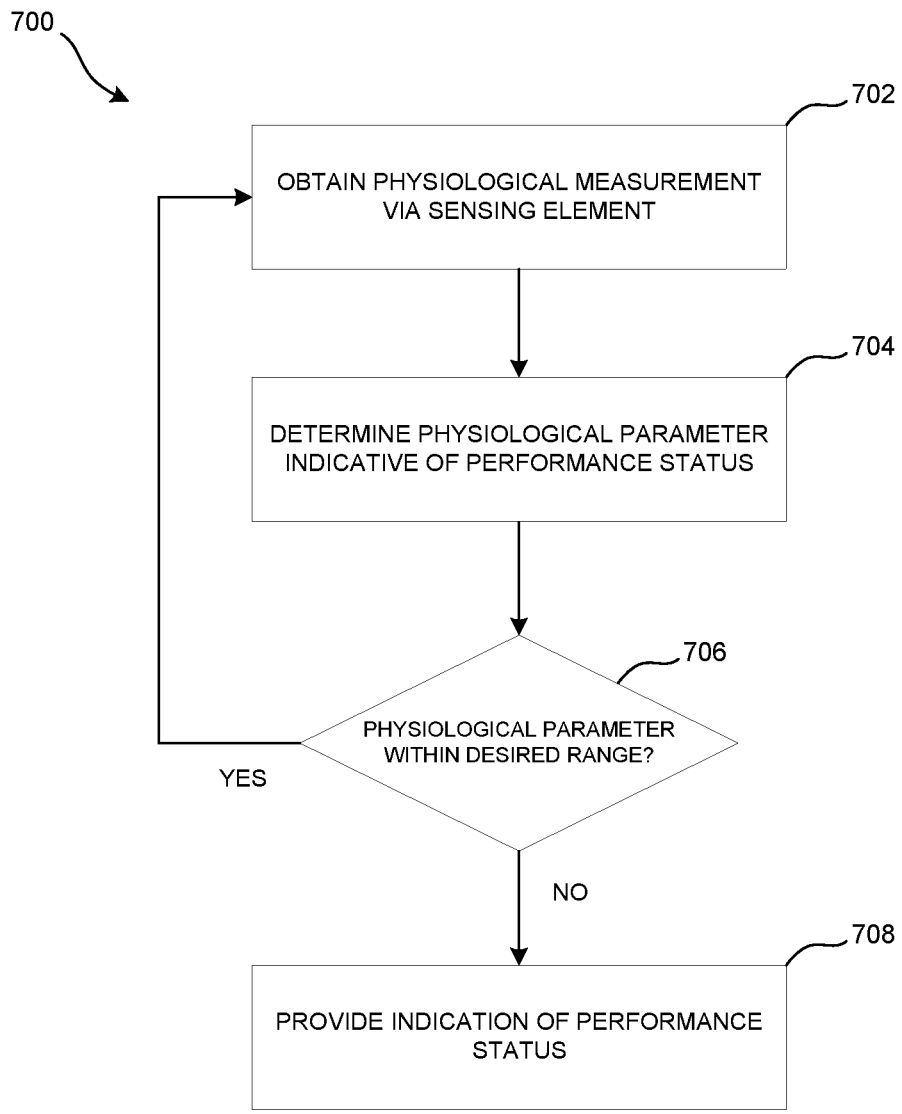
FIG. 7 is a flow diagram of a process configured to determine one or more physiological parameters and provide an indication of performance status in accordance with the present technology.

FIG. 7 shows a process 700 configured to determine a movement parameter and provide an indication of performance status or activity level to the patient and/or physician. The process 700 can be implemented by one or more aspects of the system of the present technology (such as system 10). In some embodiments, the process 700 comprises one or more instructions stored in memory (e.g., the memory of the device 100 and/or the memory of the sensing element 110) and executed by one or more processors (e.g., the controller 112, the controller of the sensing element 110, a processor of the local computing device 150 (FIG. 1), a processor of the remote computing device(s) 160, and/or a processor of the remote computing device(s) 170) of a monitoring system (e.g., system 10).

Various embodiments of the process 700 include one or more operations, functions, and actions illustrated by blocks 702 through 708. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

In addition, for the process 700 and other processes and methods disclosed herein, the flowchart shows functionality and operation of one possible implementation of some embodiments. In this regard, each block may represent a module, a segment, or a portion of program code, which includes one or more instructions executable by one or more processors for implementing specific logical functions or steps in the process. The program code may be stored on any type of computer readable medium, for example, such as a storage device including a disk or hard drive. The computer readable medium may include non-transitory computer readable media, for example, such as tangible, non-transitory computer-readable media that stores data for short periods of time like register memory, processor cache, and Random-Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the process 700 and other processes and methods disclosed herein, each block in FIG. 7 may represent circuitry that is wired to perform the specific logical functions in the process.

At block 702, the process 700 obtains physiological measurements via a sensing element (such as any of the sensing elements 110 described herein) coupled to a vascular access device (such as any of the vascular access devices 100 described herein) while the device is implanted within the patient. The sensing element 110, for example, may include an accelerometer or other sensor configured to detect and/or measure movement (or derivatives thereof), and the physiological measurements may include at least movement of the patient. The process 700 may also include measurements obtained by one or more movement detection elements positioned or worn at locations on the patient's body separate from the device 100 (as described above with respect to sepsis).

Based on the physiological measurements, the process 700 may determine at least one movement parameter. For example, the process 700 may determine a movement parameter such as (a) distance moved by the patient, (b) distance moved by the patient over a predetermined amount of time, (c) speed of movement, (d) acceleration of movement (e) distance, speed, or acceleration of movement during certain times of the day, (f) step count, (g) gait, (h) balance, direction of movement, (i) energy expended through movement, (j) caloric burn, etc. In some embodiments, the movement parameter may include distance moved, speed of movement, acceleration, and/or direction of movement by one or more extremities or portions of the patient's body (such as a torso, leg, arm, head, hand, finger, foot, toe, etc.). Such parameters may be particularly useful for identifying patient motions indicative of a disease state. For example, short, repeated, highly accelerated movements detected at the chest, head, or neck of the patient may be used to determine the patient is vomiting. In the case of a fracture or chronic pain, less or no movement of a particular region or extremity may be used to determine that the patient has a fracture or chronic pain at or near that region.

Based on the determined movement parameters, the process 700 may determine a performance status and indicate the performance status to the patient and/or physician (as shown at block 708). For example, using the aforementioned ECOG Scale, if the process 700 determines a movement parameter of less than 20 feet traveled over a 24-hour period, the process 700 may indicate a performance status grade of "3." Thresholds for different levels of performance status may be based on the patient's baseline activity level and/or an age- or medical condition-adjusted activity level. The recommended number of steps per day is 10,000, though Americans average about 5,000-7,000 steps per day. In some embodiments, the performance status grade ("PSG") may be relative to the activity level of an average, healthy individual within a given geographic area and/or age group (i.e., the PSG=0 for such an individual). On such a scale, the following thresholds and corresponding PSG's may apply: for 3,000-4,000 steps per day, PSG=1; for 2,000-3,000 steps per day, PSG=2; for 1,000-2,000 steps per day, PSG=3; for less than 1,000 steps per day, PSG=4. Thresholds based on movement parameters other than step count may also be utilized. Additionally or alternatively, the PSG may be relative to a particular patient's baseline activity level, such that a PSG of 0 is the patient's baseline activity level, and a 0-25% reduction in activity is a PSG of 1, a 25-50% reduction in activity is a PSG of 2, a 50-75% reduction in activity is a PSG of 3, and a greater than 75% reduction in activity is a PSG of 4. As used herein, "activity" and/or "activity level" may be determined based on one or more of the movement parameters. It will be appreciated that other scales may be utilized.

In some embodiments, the performance status may be based on a combination of one or more movement parameters and one or more other physiological parameters, such as a heart rate parameter, a temperature parameter, a respiratory rate parameter, a blood oxygen saturation parameter, etc. Utilizing a combination of parameters may provide a more complete or informed evaluation of the patient's health, especially to the extent that the combination of parameters indicates the intensity or vigor of physical activity. For example, a patient that is active for only 30 minutes but exhibits physiological parameters indicative of high intensity interval training (e.g., increased heart rate, respiratory rate, temperature, etc.) would be given a higher performance status than a patient that is walking to the bathroom and back over the course of an hour, even though the first patient was moving for a shorter duration.

D. Acute Myocardial Infarction ("Acute MI")

Figure 8:
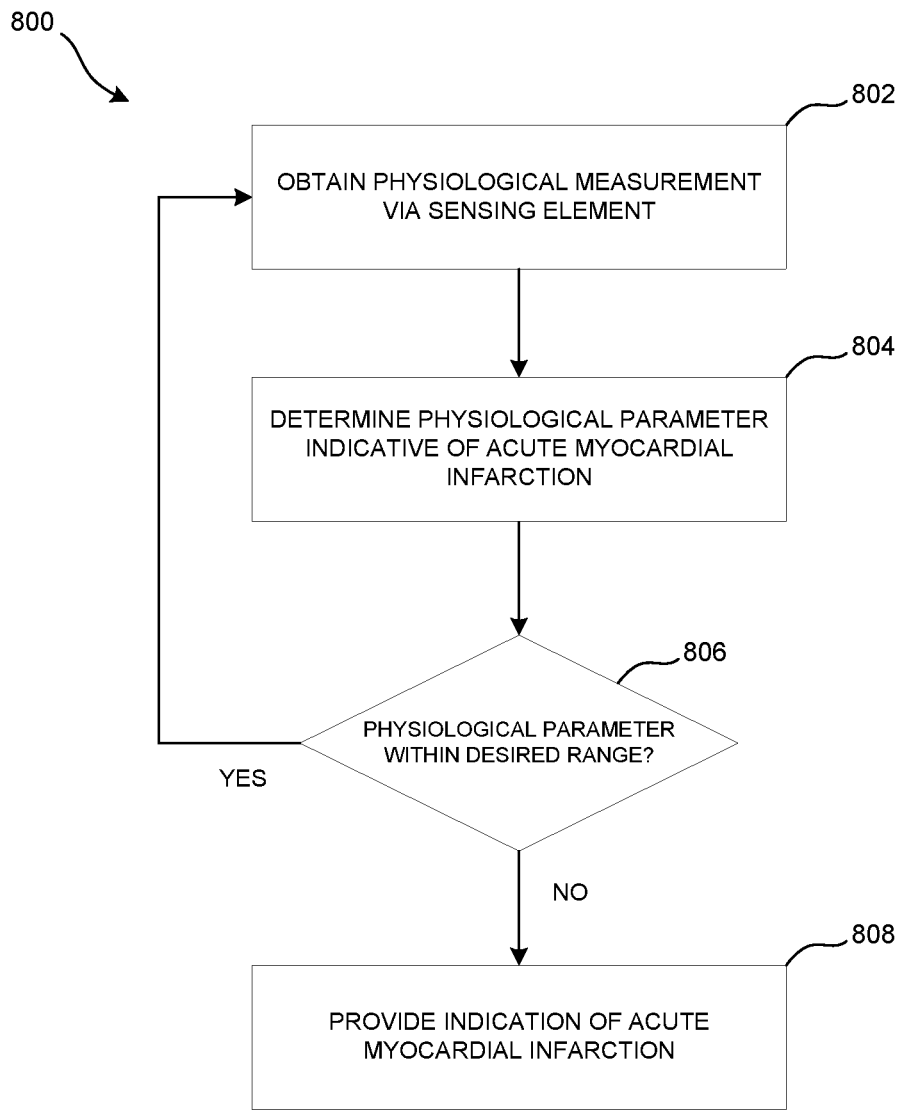
FIG. 8 is a flow diagram of a process configured to determine one or more physiological parameters and provide an indication of acute myocardial infarction in accordance with the present technology.

FIG. 8 shows a process 800 configured to determine one or more physiological parameters characterizing acute MI (and/or one or more corresponding symptoms) and provide an indication of acute MI to the patient and/or physician. The process 800 can be implemented by one or more aspects of the system of the present technology (such as system 10). In some embodiments, the process 800 comprises one or more instructions stored in memory (e.g., the memory of the device 100 and/or the memory of the sensing element 110) and executed by one or more processors (e.g., the controller 112, the controller of the sensing element 110, a processor of the local computing device 150 (FIG. 1), a processor of the remote computing device(s) 160, and/or a processor of the remote computing device(s) 170) of a monitoring system (e.g., system 10).

Various embodiments of the process 800 include one or more operations, functions, and actions illustrated by blocks 802 through 808. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

In addition, for the process 800 and other processes and methods disclosed herein, the flowchart shows functionality and operation of one possible implementation of some embodiments. In this regard, each block may represent a module, a segment, or a portion of program code, which includes one or more instructions executable by one or more processors for implementing specific logical functions or steps in the process. The program code may be stored on any type of computer readable medium, for example, such as a storage device including a disk or hard drive. The computer readable medium may include non-transitory computer readable media, for example, such as tangible, non-transitory computer-readable media that stores data for short periods of time like register memory, processor cache, and Random-Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the process 800 and other processes and methods disclosed herein, each block in FIG. 8 may represent circuitry that is wired to perform the specific logical functions in the process.

At block 802, the process 800 obtains physiological measurements via a sensing element (such as any of the sensing elements 110 described herein) coupled to a vascular access device (such as any of the vascular access devices 100 described herein) while the device is implanted within the patient. The sensing element 110 may comprise at least one electrode, and the physiological measurements may include at least electrical activity (e.g., current, voltage, impedance, etc.). Based on the physiological measurements, the process 800 may determine at least one physiological parameter indicative of acute MI (block 804), such as at least one of an ECG/EKG parameter, a respiratory rate parameter, and an activity level parameter, each of which is discussed in greater detail below.

A common symptom of acute MI is an abnormal ECG/EKG. As used herein, "abnormal ECG/EKG" refers to an ECG/EKG having at least some segments that deviate from the ECG/EKG readings of a healthy individual. Patients having an acute MI will often show ST segment elevation on ECG tracings, inverted T waves, or arrhythmias such as heart block or ventricular fibrillation. Accordingly, the system of the present technology is configured to determine an ECG/EKG parameter and compare the ECG/EKG parameter to a predetermine threshold, such as a baseline ECG/EKG of the patient or an ECG/EKG reading characterizing healthy or normal electrical activity. As shown in FIG. 8, if the process 800 determines at block 806 that the ECG/EKG parameter is outside of the predetermined threshold, then the process 800 may provide an indication that the patient has acute MI.

In addition to abnormal ECG/EKG, the process 800 may also determine one or more additional physiological parameters indicative of acute MI, such as: (a) a respiratory rate greater than baseline or other predetermined threshold (acute MI is often associated with shortness of breath which would be detected as increased respiratory rate), (b) oxygen saturation less than baseline or other predetermined threshold, and (c) performance status and/or movement outside of predetermined movement profile and/or activity level less than baseline or predetermined threshold. For example, patients with acute MI may show a sudden decrease in activity level, exhibit a "slumping" position/motion, and/or develop syncope. The sensing element 110, for example, may include one or more accelerometers and/or the system 10 may include one or more movement detection elements (described above with respect to sepsis and performance status) positioned or worn at various locations on the patient's body. The process 800 may determine that the movements obtained by the sensing element 110 characterize known movements, such as slumping or fainting. Fainting, for example, may be detected as movement indicative of a fall followed by lack of motion.

Other physiological parameters that may be determined by the process 800 and/or used to provide an indication of acute MI include: blood creatine kinase ("CK") levels greater than baseline or other predetermined threshold, blood creatine-kinase-muscle/brain ("CK-MB") levels greater than baseline or other predetermined threshold; blood troponin levels (levels) greater than baseline or other predetermined threshold, a CVP greater than baseline or other predetermined threshold, and/or high or low blood pressure.

E. Hyperglycemia/Diabetic Ketoacidosis

Figure 9:
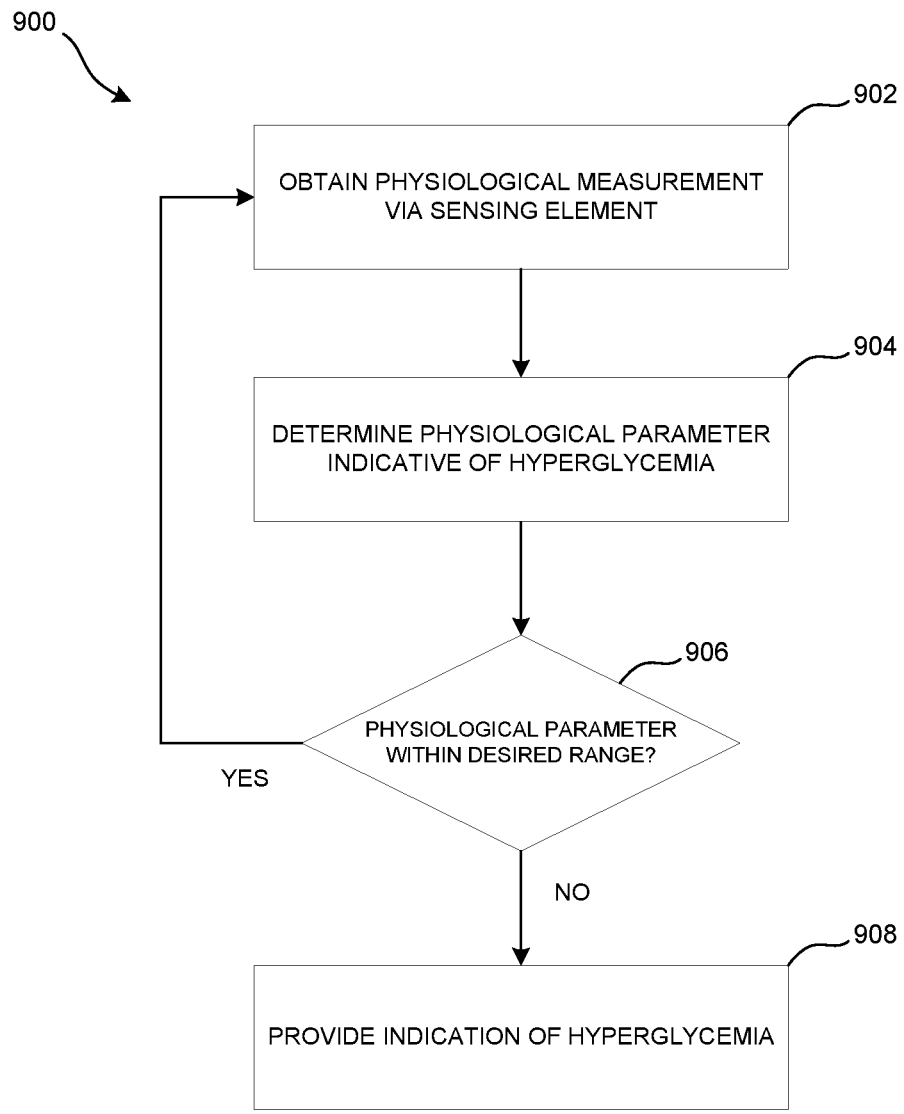
FIG. 9 is a flow diagram of a process configured to determine one or more physiological parameters and provide an indication of hyperglycemia in accordance with the present technology.

FIG. 9 shows a process 900 configured to determine one or more physiological parameters characterizing hyperglycemia/diabetic ketoacidosis (and/or one or more corresponding symptoms) and provide an indication of the same to the patient and/or physician. The process 900 can be implemented by one or more aspects of the system of the present technology (such as system 10). In some embodiments, the process 900 comprises one or more instructions stored in memory (e.g., the memory of the device 100 and/or the memory of the sensing element 110) and executed by one or more processors (e.g., the controller 112, the controller of the sensing element 110, a processor of the local computing device 150 (FIG. 1), a processor of the remote computing device(s) 160, and/or a processor of the remote computing device(s) 170) of a monitoring system (e.g., system 10).

Various embodiments of the process 900 include one or more operations, functions, and actions illustrated by blocks 902 through 908. Although the blocks are illustrated in sequential order, these blocks may also be performed in parallel, and/or in a different order than the order disclosed and described herein. Also, the various blocks may be combined into fewer blocks, divided into additional blocks, and/or removed based upon a desired implementation.

In addition, for the process 900 and other processes and methods disclosed herein, the flowchart shows functionality and operation of one possible implementation of some embodiments. In this regard, each block may represent a module, a segment, or a portion of program code, which includes one or more instructions executable by one or more processors for implementing specific logical functions or steps in the process. The program code may be stored on any type of computer readable medium, for example, such as a storage device including a disk or hard drive. The computer readable medium may include non-transitory computer readable media, for example, such as tangible, non-transitory computer-readable media that stores data for short periods of time like register memory, processor cache, and Random-Access Memory (RAM). The computer readable medium may also include non-transitory media, such as secondary or persistent long-term storage, like read only memory (ROM), optical or magnetic disks, compact-disc read only memory (CD-ROM), for example. The computer readable media may also be any other volatile or non-volatile storage systems. The computer readable medium may be considered a computer readable storage medium, for example, or a tangible storage device. In addition, for the process 900 and other processes and methods disclosed herein, each block in FIG. 9 may represent circuitry that is wired to perform the specific logical functions in the process.

At block 902, the process 900 obtains physiological measurements via a sensing element (such as any of the sensing elements 110 described herein) coupled to a vascular access device (such as any of the vascular access devices 100 described herein) while the device is implanted within the patient. The sensing element 110 may include, for example, an electrode and/or an electro-optical sensor (such as a pulse oximeter). Based on the physiological measurements, the process 900 may determine at least one physiological parameter indicative of hyperglycemia/diabetic ketoacidosis (block 904), such as at least one of a heart rate parameter, a respiratory rate parameter, and an ECG/EKG parameter, each of which is discussed in greater detail below.

A common symptom of hyperglycemia/diabetic ketoacidosis is tachycardia, or increased heart rate. Accordingly, the system of the present technology is configured to determine a heart rate parameter, such as a heart rate of the patient. As shown in FIG. 9, if the process 900 determines at block 906 that the heart rate parameter is outside of a corresponding predetermined threshold, then the process 900 may provide an indication that the patient is hyperglycemic. For example, the process 900 may provide an indication that the patient is hyperglycemic if the process 900 determines: (a) the heart rate of the patient is greater than 90, 95, or 100 beats per minute; (b) the heart rate of the patient is greater than 90, 95, or 100 beats per minute for a predetermined amount of time; (c) the heart rate of the patient increases at least 10%, 15%, or 20% from a reference heart rate of the patient; and/or (d) the heart rate of the patient increases at least 10%, 15%, or 20% from a reference heart rate of the patient over a predetermined amount of time.

Another common symptom of hyperglycemia/diabetic ketoacidosis is increased respiratory rate. Accordingly, the system of the present technology is configured to determine a respiratory rate parameter, such as a respiratory rate of the patient. As shown in FIG. 9, if the process 900 determines at block 906 that the respiratory rate parameter is outside of a corresponding predetermined threshold, then the process 900 may provide an indication that the patient is hyperglycemic. For example, the process 900 may provide an indication that the patient is hyperglycemic if the process 900 determines (a) the respiratory rate of the patient is greater than 15 breaths per minute, and/or (b) the respiratory rate of the patient is greater than 15 breaths per minute for a predetermined amount of time.

Another common symptom of hyperglycemia/diabetic ketoacidosis is abnormal electrical activity of the heart, for example as indicated by an abnormal ECG/EKG. For example, the process 900 may be configured to provide an indication that the patient is hyperglycemic if the process 900 determines an ECG/EKG parameter with traits suggestive of hyperglycemia, such as peaked T waves in hyperkalemia, U waves in hypokalemia, QT prolongation in hypokalemia, hypocalcemia, and hypomagnesemia, and QT shortening in hyperkalemia and hypercalcemia. These abnormalities in ECG/EKG are typically the result of severe electrolyte abnormalities associated with hyperglycemia/diabetic ketoacidosis that affect the patient's heart rhythm and cause arrhythmias.

Other physiological parameters that may be determined by the process 900 and/or used to provide an indication of hyperglycemia/diabetic ketoacidosis include: blood glucose greater than baseline or other predetermined threshold (usually highly elevated); blood potassium levels greater than baseline or other predetermined threshold; blood calcium levels less than baseline or other predetermined threshold; BUN levels greater than baseline or other predetermined threshold and/or blood creatinine levels greater than baseline or other predetermined threshold (elevated BUN and blood creatinine levels are indicative of renal dysfunction); blood ketone levels greater than baseline or other predetermined threshold; blood pH less than baseline or predetermined threshold; low blood pressure; and/or one or more of the physiological parameters discussed above with respect to sepsis.

F. Additional Medical Conditions

The devices, systems, and methods of the present technology may also be configured to detect or provide an indication of one or more other medical conditions. As used in relation to any of the medical conditions discussed herein, "provide an indication of a [medical condition]" includes an indication that the patient is developing or at risk of developing the medical condition, as well as an indication that the patient has already developed the medical condition. For example, in some embodiments, the system is configured to determine one or more physiological parameters indicative of gastroparesis/cyclic vomiting syndrome and provide an indication of gastroparesis/cyclic vomiting syndrome. For example, the system may provide an indication of gastroparesis/cyclic vomiting syndrome based on determining: heart rate greater than baseline or other predetermined threshold; movement outside of predetermined movement profile and/or activity level less than baseline or predetermined threshold; generalized weakness and decreased activity; detection of movements indicative of vomiting, low blood pressure; multiple electrolyte abnormalities (usually due to vomiting); and/or one, some, or all of the physiological parameters discussed above with respect to dehydration.

In some embodiments, the system is configured to determine one or more physiological parameters indicative of hemophilia and provide an indication of hemophilia. For example, the system may provide an indication of hemophilia based on determining: heart rate greater than baseline or other predetermined threshold and/or movement outside of predetermined movement profile and/or activity level less than baseline or predetermined threshold, especially such movements that are indicative of generalized weakness and decreased activity.

In some embodiments, the system is configured to determine one or more physiological parameters indicative of cystic fibrosis and provide an indication of cystic fibrosis. For example, the system may provide an indication of cystic fibrosis based on determining: heart rate greater than baseline or other predetermined threshold; oxygen saturation less than baseline or other predetermined threshold; and/or one or more physiological parameters for infection/sepsis, detailed above.

In some embodiments, the system is configured to determine one or more physiological parameters indicative of chronic pain and provide an indication of chronic pain. For example, the system may provide an indication of chronic pain based on determining: heart rate greater than baseline or other predetermined threshold; movement outside of predetermined movement profile and/or activity level less than baseline or predetermined threshold; and/or one, some, or all of the physiological parameters discussed above with respect to opioid abuse.

In some embodiments, the system is configured to determine one or more physiological parameters indicative of a seizure and provide an indication of a seizure. For example, the system may provide an indication of a seizure based on determining, for example: movement outside of predetermined movement profile and/or activity level less than baseline or predetermined threshold; characteristic repetitive motion of tonic/clonic (grand mal) seizure activity, a heart rate greater than baseline or other predetermined threshold; abnormal ECG/EKG parameter relative to a predetermined profile or pattern; respiratory rate less than or outside of baseline or other predetermined threshold (as a patient's breathing is often decreased, erratic, or arrested during seizure); oxygen saturation less than baseline or other predetermined threshold; and/or electrolyte abnormalities in the blood (such as those discussed above).

In some embodiments, the system is configured to determine one or more physiological parameters indicative of pulmonary embolism ("PE") and provide an indication of PE. For example, the system may provide an indication of PE based on determining: heart rate greater than a baseline value or range or other predetermined threshold; oxygen saturation less than baseline or other predetermined threshold; the combination of increased heart rate and decreased oxygen saturation are especially indicative of PE; fall and/or movement/activity level (patients with a massive PE may have syncope which would be detected as movement indicative of a fall followed by lack of motion); D Dimer (blood parameter that is seen in hypercoagulable states such as deep vein thrombosis and PE); central venous pressure greater than baseline or other predetermined threshold (PE can cause right heart strain, which then elevates central venous pressure); and/or systemic blood pressure less than baseline or other predetermined threshold.

In some embodiments, the system is configured to determine one or more physiological parameters indicative of metastatic spinal cord compression and provide an indication of metastatic spinal cord compression. For example, the system may provide an indication of metastatic spinal cord compression based on determining: movement outside of predetermined movement profile and/or activity level less than baseline or predetermined threshold (spinal cord compression often leads to leg weakness or paralysis; this may be detected as either a gait change/limp, or a complete lack of walking in the case of paralysis) and/or heart rate greater than baseline or other predetermined threshold (for example, due to pain and increased work of movement with weakened legs).

In some embodiments, the system is configured to determine one or more physiological parameters indicative of anemia and provide an indication of anemia. For example, the system may provide an indication of anemia based on determining: Heart rate greater than baseline or other predetermined threshold; respiratory rate greater than baseline or other predetermined threshold; hemoglobin level less than baseline or other predetermined threshold; hematocrit less than baseline or other predetermined threshold; and/or RBC count less than baseline or other predetermined threshold.

In some embodiments, the system is configured to determine one or more physiological parameters indicative of dehydration/volume depletion and provide an indication of dehydration/volume depletion. For example, the system may provide an indication of dehydration/volume depletion based on determining: heart rate greater than baseline or other predetermined threshold; movement outside of baseline movement profile and/or activity level less than baseline or predetermined threshold; central venous pressure less than baseline or other predetermined threshold; systemic blood pressure less than baseline or other predetermined threshold; and/or blood pH less than baseline or predetermined threshold.

In some embodiments, the system is configured to determine one or more physiological parameters indicative of vomiting and provide an indication of vomiting. For example, the system may provide an indication of vomiting based on determining: movement outside of predetermined movement profile and/or activity level less than baseline or predetermined threshold (the act of vomiting has characteristic motions that can be detected with, for example, one or more accelerometers); and/or physiological parameters for dehydration, detailed above.

In some embodiments, the system is configured to determine one or more physiological parameters indicative of pneumonia and provide an indication of pneumonia. For example, the system may provide an indication of pneumonia based on determining: Temperature parameter greater than baseline or other predetermined threshold; heart rate greater than baseline or other predetermined threshold; oxygen saturation less than baseline or other predetermined threshold; movement outside of predetermined movement profile and/or activity level less than baseline or predetermined threshold (patients with pneumonia become lethargic and therefore less active, and movements indicative of heavy coughing typically seen in pneumonia may be detected); respiratory rate greater than baseline or other predetermined threshold; white blood cell count greater than baseline or other predetermined threshold; lactic acid greater than baseline or other predetermined threshold; procalcitonin greater than baseline or other predetermined threshold; and/or one or more of the physiological parameters for sepsis, detailed above (pneumonia can develop into sepsis).

In some embodiments, the system is configured to determine one or more physiological parameters indicative of arrhythmia and provide an indication of arrhythmia. For example, the system may provide an indication of arrhythmia based on determining: abnormal ECG/EKG parameter relative to a predetermined profile or pattern; heart rate greater than baseline or other predetermined threshold; heart rate less than baseline or other predetermined threshold; irregular heart rhythm; a fall and/or movement/activity level (patients with an arrythmia may have syncope which would be detected as movement indicative of a fall followed by lack of motion); central venous pressure greater than baseline or other predetermined threshold; and/or high or low blood pressure.

In some embodiments, the system is configured to determine one or more physiological parameters indicative of neutropenic fever/sepsis and provide an indication of neutropenic fever/sepsis. For example, the system may provide an indication of neutropenic fever/sepsis based on determining: a temperature parameter greater than predetermined threshold (e.g., elevated over 100 or 2% over baseline; heart rate greater than baseline or other predetermined threshold (normal heart rate ranges from 60-100 beats per minute (BPM) but can vary between individuals; typically in sepsis heart rate rises above 100 BPM or an increase in reference heart rate by 20%); white blood cell count less than baseline or other predetermined threshold; absolute neutrophil count under 1,000/mm³; and/or one or more of the physiological parameters for sepsis, detailed above.

In some embodiments, the system is configured to determine one or more physiological parameters indicative of pain and provide an indication of pain. For example, the system may provide an indication of pain based on determining: heart rate greater than baseline or other predetermined threshold (increasing or uncontrolled pain causes an increase in heart rate); movement outside of predetermined movement profile and/or activity level less than baseline or predetermined threshold; patients in pain will move less, may develop gait abnormalities to compensate for pain, or exhibit characteristic body positioning to relive pain; and/or respiratory rate greater than baseline or other predetermined threshold.

In some embodiments, the system is configured to determine one or more physiological parameters indicative of opioid toxicity, or other dependency, and provide an indication of opioid toxicity, or other drug dependency. For example, the system may provide an indication of opioid toxicity based on determining: respiratory rate less than baseline or other predetermined threshold; oxygen saturation less than baseline or other predetermined threshold (with severe opioid induced respiratory depression, patients often develop low oxygen saturation); movement outside of predetermined movement profile and/or activity level less than baseline or predetermined threshold (as patients become sedated they may develop rapidly decreasing activity or may develop syncope, which could be detected by movements indicative of a fall, as discussed above); abnormal EKG/ECG (in advanced stages of opioid toxicity, patients may develop arrhythmia); and/or low blood pressure.

In some embodiments, the system is configured to determine one or more physiological parameters indicative of hypoglycemia and provide an indication of hypoglycemia. For example, the system may provide an indication of hypoglycemia based on determining: heart rate greater than baseline or other predetermined threshold; respiratory rate less than baseline or other predetermined threshold (respiratory rate may be low in comatose state); movement outside of predetermined movement profile and/or activity level less than baseline or predetermined threshold; severe hypoglycemia can cause coma/loss of consciousness and even seizures; blood glucose less than baseline or other predetermined threshold; low blood pressure; and/or physiological parameters for sepsis, detailed above (hypoglycemia often has co-existing infection).

In some embodiments, the system is configured to determine one or more physiological parameters indicative of hyperkalemia and provide an indication of hyperkalemia. For example, the system may provide an indication of hyperkalemia based on determining: abnormal ECG/EKG parameter relative to a predetermined profile or pattern (for example, characteristic "peaked" or very tall P waves; as potassium rises, intervals widen and changes progress to "sine wave" morphology; with severe hyperkalemia, can have arrhythmias, heart block, asystole); movement outside of predetermined movement profile and/or activity level less than baseline or predetermined threshold (such as that indicative of cardiac arrest, decreased motor strength, paralysis, and/or decreased activity); serum potassium greater than baseline or other predetermined threshold; blood urea nitrogen ("BUN") levels greater than baseline or other predetermined threshold and/or blood creatinine levels greater than baseline or other predetermined threshold (these two parameters are indicative of renal dysfunction); blood magnesium levels greater than baseline or predetermined threshold; blood phosphorus levels greater than baseline or predetermined threshold; and/or blood digoxin levels greater than baseline or predetermined threshold.

In some embodiments, the system is configured to determine one or more physiological parameters indicative of hypercalcemia and provide an indication of hypercalcemia. For example, the system may provide an indication of hypercalcemia based on determining: abnormal ECG/EKG relative to a predetermined profile or pattern (for example, characteristic QT interval shortening); movement outside of predetermined movement profile and/or activity level less than baseline or predetermined threshold; severe hypercalcemia can lead to muscle weakness, and even lead to confusion, coma; serum calcium greater than baseline or other predetermined threshold; blood magnesium levels greater than baseline or predetermined threshold; blood phosphorus levels greater than baseline or predetermined threshold; can have additional electrolyte abnormalities (magnesium, potassium); and/or BUN levels greater than baseline or other predetermined threshold and/or blood creatinine levels greater than baseline or other predetermined threshold (elevated BUN and blood creatinine levels are indicative of renal dysfunction, which is often seen in cancer patients with either extensive bone metastases or paraneoplastic syndromes).

In some embodiments, the system is configured to determine one or more physiological parameters indicative of hyponatremia and provide an indication of hyponatremia. For example, the system may provide an indication of hyponatremia based on determining: heart rate greater than baseline or other predetermined threshold (for example, can be elevated if dehydrated); respiratory rate greater than baseline or other predetermined threshold (may be low in comatose state); movement outside of predetermined movement profile and/or activity level less than baseline or predetermined threshold; severe hyponatremia can cause confusion, lethargy, seizures, and coma; low serum sodium. Multiple causes, such as excess water intake, hypovolemia, SIADH (syndrome of inappropriate anti-diuretic hormone), excess use of diuretic medication; BUN levels greater than baseline or other predetermined threshold and/or blood creatinine levels greater than baseline or other predetermined threshold. (These two parameters are indicative of renal dysfunction. Renal dysfunction is especially relevant if hyponatremia is due to dehydration from medication like diuretics.); and/or thyroid dysfunction, can check blood TSH/thyroid studies.

In some embodiments, the system is configured to determine one or more physiological parameters indicative of brain metastases and provide an indication of brain metastases. For example, the system may provide an indication of brain metastases based on determining: movement outside of predetermined movement profile and/or activity level less than baseline or predetermined threshold; patients with symptomatic brain metastases will display decreased activity levels; movement(s) indicative of focal neurologic deficits may be detected, such as abnormal movements, an abnormal gait, and/or vomiting; abnormal ECG/EKG parameter relative to a predetermined profile or pattern, such as widespread T-wave inversions (known as "cerebral T waves"), QT prolongation, ST elevation or depression (mimics ischemia), and/or arrhythmias; respiratory rate greater than baseline or other predetermined threshold (increased intracranial pressure can lead to low respiratory rate or erratic breathing pattern); heart rate greater than baseline or other predetermined threshold; increased intracranial pressure can lead to bradycardia; increased or high blood pressure (for example, as a result of severe increased intracranial pressure); heart rate less than baseline or other predetermined threshold (for example, as a result of severe increased intracranial pressure); and/or irregular breathing.

In some embodiments, the system is configured to determine one or more physiological parameters indicative of superior vena cava syndrome ("SVC Syndrome") and provide an indication of SVC Syndrome. For example, the system may provide an indication of SVC Syndrome based on determining: heart rate greater than baseline or other predetermined threshold (due to a combination of pain and decreased preload, heart rate will increase in SVC syndrome); respiratory rate greater than baseline or other predetermined threshold; movement outside of predetermined movement profile and/or activity level less than baseline or predetermined threshold; and/or normal central venous pressure.

In some embodiments, the system is configured to determine one or more physiological parameters indicative of gastrointestinal hemorrhage and provide an indication of gastrointestinal hemorrhage. For example, the system may provide an indication of gastrointestinal hemorrhage based on determining: heart rate greater than baseline or other predetermined threshold (for example, due to rapid blood loss); movement outside of predetermined movement profile and/or activity level less than baseline or predetermined threshold; patients with hemorrhage will display decreased activity levels; and/or physiological parameters indicative of cardiac ischemia, such as hemoglobin levels less than baseline or other predetermined threshold and/or hematocrit less than baseline or other predetermined threshold; low blood pressure (because of severe blood loss).

In some embodiments, the system is configured to determine one or more physiological parameters indicative of immunotherapy-induced or radiation pneumonitis and provide an indication of immunotherapy-induced or radiation pneumonitis. For example, the system may provide an indication of pneumonitis based on determining, for example: oxygen saturation less than baseline or other predetermined threshold; heart rate greater than baseline or other predetermined threshold; respiratory rate greater than baseline or other predetermined threshold; temperature parameter greater than predetermined threshold, or normal movement outside of predetermined movement profile and/or activity level less than baseline or predetermined threshold; including detecting motions indicative of heavy coughing; and/or elevated levels of inflammatory markers, including cytokines (interleukins, tumor necrosis factor ("TNF"), C reactive protein, and erythrocyte sedimentation rate).

In some embodiments, the system is configured to determine one or more physiological parameters indicative of immunotherapy-induced colitis and provide an indication of immunotherapy-induced colitis. For example, the system may provide an indication of immunotherapy-induced colitis based on determining, for example: heart rate greater than baseline or other predetermined threshold; respiratory rate greater than baseline or other predetermined threshold; temperature parameter greater than baseline or other predetermined threshold, or normal movement outside of predetermined movement profile and/or activity level less than baseline or predetermined threshold; and/or elevated levels of inflammatory markers including cytokines (interleukins, TNF, C reactive protein, erythrocyte sedimentation rate).

In some embodiments, the system is configured to determine one or more physiological parameters indicative of diarrhea and provide an indication of diarrhea. For example, the system may provide an indication of diarrhea based on determining, for example: heart rate greater than baseline or other predetermined threshold; temperature parameter greater than baseline or other predetermined threshold; movement outside of predetermined movement profile and/or activity level less than baseline or predetermined threshold; multiple lab abnormalities including altered renal function (BUN/creatinine) from dehydration, abnormal potassium, sodium, and acidosis; and/or low blood pressure, especially if severe volume loss with diarrhea.

In some embodiments, the system is configured to determine one or more physiological parameters indicative of a cerebrovascular accident ("CVA") and provide an indication of a CVA. For example, the system may provide an indication of a CVA based on determining, for example: movement outside of predetermined movement profile and/or activity level less than baseline or predetermined threshold (patients with CVA will display sudden focal neurologic deficits that may be detected as movement or gait disorders); respiratory rate greater than baseline or other predetermined threshold; increased intracranial pressure can lead to low respiratory rate or erratic breathing pattern; heart rate less than baseline or other predetermined threshold; and/or high or increased blood pressure.

In some embodiments, the system is configured to determine one or more physiological parameters indicative of a pathologic fracture and provide an indication of a pathologic fracture. For example, the system may provide an indication of a pathologic fracture based on determining, for example, movement outside of predetermined movement profile and/or activity level less than baseline or predetermined threshold (patients with a pathologic fracture will develop sudden decrease in activity level as well as gait disorders if they remain ambulatory).

In some embodiments, the system is configured to determine one or more physiological parameters indicative of hemoptysis or hematemesis and provide an indication of the same. For example, the system may provide an indication of hemoptysis or hematemesis based on determining, for example: heart rate greater than baseline or other predetermined threshold; movement outside of predetermined movement profile and/or activity level less than baseline or predetermined threshold; hemoglobin level less than baseline or other predetermined threshold; hematocrit less than baseline or other predetermined threshold; and/or low blood pressure. Detection of excessive vomiting (indicative of hemoptysis or hematemesis) may be determined via detecting one or more movements indicative of vomiting, alone or in combination with: (a) one or more electrolyte abnormalities, such as blood potassium levels greater than baseline or other predetermined threshold and blood calcium levels less than baseline or other predetermined threshold); (b) renal dysfunction from dehydration (e.g., by determining BUN levels greater than baseline or other predetermined threshold and/or blood creatinine levels greater than baseline or other predetermined threshold).

In some embodiments, the system is configured to determine one or more physiological parameters indicative of a medication-induced QT prolongation and provide an indication of the same. For example, the system may provide an indication of a medication-induced QT prolongation based on determining, for example: abnormal ECG/EKG parameter relative to a predetermined profile or pattern (such as prolongation of the QT interval on ECG that can lead to ventricular arrhythmias and cardiac arrest); movement outside of predetermined movement profile and/or activity level less than baseline or predetermined threshold (especially detection of movement indicative of syncope or cardiac arrest); and/or electrolyte abnormalities, such as blood potassium levels greater than baseline or other predetermined threshold; blood calcium levels less than baseline or other predetermined threshold.

In some embodiments, the system is configured to determine one or more physiological parameters indicative of a heart block and provide an indication of a heart block. For example, the system may provide an indication of a heart block based on determining, for example: abnormal ECG/EKG parameter relative to a predetermined profile or pattern; characteristic changes in PR interval seen in different degrees of heart block; heart rate less than baseline or other predetermined threshold; movement outside of predetermined movement profile and/or activity level less than baseline or predetermined threshold; heart block can lead to syncope which would be detected as a fall; oxygen saturation less than baseline or other predetermined threshold (especially if heart block leads to CHF); respiratory rate greater than baseline or other predetermined threshold; and/or central venous pressure greater than baseline or other predetermined threshold.

In some embodiments, the system is configured to determine one or more physiological parameters indicative of a tumor lysis syndrome and provide an indication of tumor lysis syndrome. For example, the system may provide an indication of tumor lysis syndrome based on determining, for example: abnormal ECG/EKG parameter relative to a predetermined profile or pattern; movement outside of predetermined movement profile and/or activity level less than baseline or predetermined threshold (i.e., generalized lethargy and decreased activity); blood potassium levels greater than baseline or other predetermined threshold; blood calcium levels less than baseline or other predetermined threshold; may have phosphorus abnormalities; BUN levels greater than baseline or other predetermined threshold and/or blood creatinine levels greater than baseline or other predetermined threshold (elevated BUN and blood creatinine levels are indicative of renal dysfunction); physiological parameters for dehydration, detailed above; elevated white blood cell count, elevated lactate dehydrogenase ("LDH"), and/or elevated uric acid.

In some embodiments, the system is configured to determine one or more physiological parameters indicative of a sickle cell anemia crisis and provide an indication of sickle cell anemia crisis. For example, the system may provide an indication of sickle cell anemia crisis based on determining, for example: heart rate greater than baseline or other predetermined threshold; movement outside of predetermined movement profile and/or activity level less than baseline or predetermined threshold (i.e., generalized weakness and decreased activity, or movements indicative or a seizures); hemoglobin level less than baseline or other predetermined threshold; hematocrit less than baseline or other predetermined threshold; reticulocyte count; BUN levels greater than baseline or other predetermined threshold and/or blood creatinine levels greater than baseline or other predetermined threshold (elevated BUN and blood creatinine levels are indicative of renal dysfunction); and/or physiological parameters for sepsis, detailed above (sickle cell patients often have splenectomy and are at risk for certain bacterial infections).

III. Conclusion

Although many of the embodiments are described above with respect to systems, devices, and methods for obtaining physiological measurements and/or determining physiological parameters via a vascular access device, the technology is applicable to other applications, forms, and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above.

The above detailed descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method for remotely monitoring the health of a patient undergoing cancer therapy, the method comprising:

obtaining physiological measurements via a sensing element of a vascular access device while the vascular access device is implanted within the patient, the vascular access device comprising a housing containing (a) a reservoir, and (b) a septum adjacent the reservoir, wherein the septum is configured to receive a needle therethrough for delivery of a fluid agent to the reservoir, and wherein the sensing element is carried by the housing;

determining at least three physiological parameters based on the physiological measurements, wherein the at least three physiological parameters include (a) a temperature parameter, (b) an activity level parameter, and (c) at least one of a heart rate parameter and a respiratory rate parameter, and wherein the activity level parameter characterizes movement of the patient;

comparing the temperature parameter to a predetermined temperature threshold;

comparing the activity level parameter to a predetermined activity level threshold, wherein the predetermined activity level threshold is based at least in part on a baseline activity level of the patient;

comparing the at least one of the heart rate parameter and the respiratory rate parameter to a predetermined heart rate threshold and a predetermined respiratory rate threshold, respectively; and based on the temperature parameter comparison, the activity level parameter comparison, and the at least one of the heart rate parameter comparison and the respiratory rate parameter comparison, providing an indication that the patient is septic to a remote computing device.

2. The method of claim 1, wherein the sensing element comprises at least one of a temperature sensing element, a heart rate sensing element, a respiratory rate sensing element, a movement sensing element, a pressure sensing element, and an electrical signal sensing element.

3. The method of claim 1, wherein the temperature parameter is a body temperature of the patient, and wherein the method further includes determining the body temperature is outside of 96-100° F.

4. The method of claim 1, wherein the temperature parameter is a body temperature of the patient, and wherein the method further includes determining the body temperature is greater than 100° F. or determining the body temperature is less than 96° F.

5. The method of claim 1, wherein the sensing element comprises a pulse oximeter.

6. The method of claim 1, wherein the heart rate parameter is a heart rate of the patient, and wherein the method further includes determining the heart rate of the patient is greater than 90 beats per minute.

7. The method of claim 1, wherein the heart rate parameter is a change in a heart rate of the patient, and wherein the method further includes determining the heart rate of the patient increases at least 10% from a reference heart rate of the patient.

8. The method of claim 1, wherein the respiratory rate parameter is a respiratory rate of the patient, and wherein the method further includes determining the respiratory rate of the patient is greater than 15 breaths per minute.

9. The method of claim 1, wherein the sensing element comprises an accelerometer.

10. The method of claim 1, wherein the activity level parameter is an amount of movement of the patient over a predetermined amount of time, and wherein the method further includes determining the activity level parameter is less than the predetermined activity level threshold.

11. The method of claim 1, wherein the sensing element is built into the housing such that only a portion of the sensing element is exposed to a local physiological environment when the device is implanted.

12. The method of claim 1, wherein the vascular access device further includes a controller, and wherein the sensing element is wired to the controller.

13. The method of claim 1, wherein the sensing element is built into the housing such that no portion of the sensing element is exposed to a local physiological environment when the device is implanted.

14. The method of claim 1, wherein determining at least three physiological parameters comprises determining at least four physiological parameters based on the physiological measurements, wherein at least one of the physiological parameters is a blood oxygen saturation parameter.

* * * * *

UNITED STATES PATENT AND TRADEMARK OFFICE
CERTIFICATE OF CORRECTION

PATENT NO. : 11,096,582 B2  
APPLICATION NO. : 16/197083  
DATED : August 24, 2021  
INVENTOR(S) : Mitchell et al.

It is certified that error appears in the above-identified patent and that said Letters Patent is hereby corrected as shown below:

On the Title Page

Item (56), in Column 2, under "Other Publications", Line 3, delete "Achive," and insert -- Archive, --, therefor.

Item (74), in Column 2, in "Attorney, Agent, or Firm", Line 1, delete "IP," and insert -- IP --, therefor.

Signed and Sealed this
Twenty-sixth Day of October, 2021

Drew Hirshfeld
*Performing the Functions and Duties of the
Under Secretary of Commerce for Intellectual Property and
Director of the United States Patent and Trademark Office*